(12) United States Patent
Bommer et al.

(10) Patent No.: US 6,573,258 B2
(45) Date of Patent: Jun. 3, 2003

(54) PHOTODYNAMIC PORPHYRIN ANTIMICROBIAL AGENTS

(75) Inventors: Jerry C. Bommer, Franklin, ID (US); Giulio Jori, Padua (IT)

(73) Assignee: Frontier Scientific, Inc., Logan, UT (US)

( * ) Notice: Subject to any disclaimer, the term of this patent is extended or adjusted under 35 U.S.C. 154(b) by 0 days.

(21) Appl. No.: 09/964,286

(22) Filed: Sep. 26, 2001

(65) Prior Publication Data

US 2003/0050296 A1 Mar. 13, 2003

Related U.S. Application Data

(60) Provisional application No. 60/235,822, filed on Sep. 27, 2000.

(51) Int. Cl.[7] ..................... A61K 31/409; C07D 487/22
(52) U.S. Cl. ....................... 514/185; 514/333; 514/338; 514/410; 540/145
(58) Field of Search .................. 540/145; 514/185, 514/333, 338, 410

(56) References Cited

FOREIGN PATENT DOCUMENTS

| DE | 199 62 505 | * | 7/2001 |
| WO | WO 93/00815 | * | 1/1993 |

OTHER PUBLICATIONS

Bonnett et al., Chemical Abstracts, vol. 119:97046, 1993.*
Schaffer et al., Chemical Abstracts, vol. 135:73949, 2001.*
Sobsey et al., Chemical Abstracts, vol. 136:90904, 2002.*
Reddi et al., Chemical Abstracts, vol. 137:105827, 2002.*
"Rapid Control of Wound Infections by Targeted Photodynamic Therapy Monitored by in vitro Bioluminiscence Imaging," Hamblin, M., *ASP Journal*, Jan. 2001, vol. 75 (1), pp. 1–25.

"Targeted Antimicrobial Photochemotherapy," Sosukos, N. et al., *Antimicrobial Agents and Chemotherapy*, Oct. 1998, pp. 2595–2601.

"Studies on the Mechanism of Bacteria Photosensitization by Meso–Substituted Cationic Porphyrins," Merchat, M. et al., *Journal of Photochemistry and Photobiology B: Biology*, 1996, vol. 35, pp. 149–157.

"Photoinactivation of Bacteria. Use of Cationic Water–Soluble Zinc Phthalocyanine to Photoinactivate Both Gram–Negative and Gram–Positive Bacteria," Minneck, A., *Journal of Photochemistry and Photobiology B: Biology*, 1996, vol 32, pp. 159–164.

"Meso–Substituted Cationic Porphyrins as Efficient Photosensitizers of Gram–Positive and Gram–Negative Bacteria," Merchat, M. et al., *Journal of Photochemistry and Photobiology B: Biology*, 1996, vol. 32, pp. 153–157.

"Inactivation of Gram–Negative Bacteria by Photosensitized Porphyrins," Nitzan, Y. et al., *Photochemistry and Photobiology*, 1992, vol. 55, No. 1, pp. 89–96.

"An Improved Synthesis of Surfactant Porphyrins," Okuno, Y. et al., *Communications*, Jul. 1980, pp. 537–539.

\* cited by examiner

*Primary Examiner*—Richard L. Raymond
(74) *Attorney, Agent, or Firm*—Madson & Metcalf (57) ABSTRACT

A series of novel positively-charged porphyrins is disclosed which exhibit a markedly increased efficiency in photosensitizing both Gram-positive and Gram-negative bacteria to the action of visible light, causing death to such bacteria when present at much lower concentrations and much shorter irradiation times than those porphyrins taught in the prior art. These porphyrins are characterized by the presence of up to four positive charges in the peripheral substituents and at least one hydrophobic tail comprising between 6 and 22 carbons inclusive, originating at one or more of the charged sites.

58 Claims, 6 Drawing Sheets

$R_1 = R_2 = R_3 = -CH_3$

| | |
|---|---|
| $R_4 = -CH_3$ | T$_4$MPyP |
| $-CH_2(CH_2)_4CH_3$ | C8 |
| $-CH_2(CH_2)_3CH_2$ | C10 |
| $-CH_2(CH_2)_{12}CH_3$ | C14 |
| $-CH_2(CH_2)_{16}CH_3$ | C16 |
| $-CH_2(CH_2)_{20}CH_3$ | C22 |

PHOTODYNAMIC PORPHYRIN ANTIMICROBIAL AGENTS

RELATED APPLICATIONS

This application is related to and claims the benefit of U.S. Provisional Patent Application Ser. No. 60/235,822 of Jerry C. Bommer and Giulio Jori, filed Sep. 27, 2000, and entitled "Photodynamic Antibacterial Agents," which is incorporated herein by reference.

BACKGROUND OF THE INVENTION

1. Field of the Invention

The present invention relates to antimicrobial agents. More specifically, the present invention relates to a series of novel positively-charged porphyrins having at least two and up to four positive charges situated in peripheral substituents of the tetrapyrrolic macrocycle and at least one hydrophobic tail originating from one of such charged sites or two adjacent charged sites which are active as photodynamic agents in killing both Gram-positive and Gram-negative bacteria.

2. Description of Related Art

The resistance to antibiotics developed by an increasing number of microorganisms is recognized to be a worldwide health problem. Tunger et al., *Int. J. Antimicrob. Agents*, 15:131–135 (2000); Jorgensen & Ferraro, *Clin. Infect. Dis.* 30:799–808 (2000). Historically, the discovery and development of new antibiotics has been a slow process plagued with uncertainty, disappointment, and only relatively rare successes. Even after discovery, prospective drug candidates must undergo rigorous testing to assure their safety and efficacy. Because of this, the highly reported advent of drug-resistant microorganisms has caused alarm among medical professionals and the public, with many left wondering whether novel antibiotics can be developed quickly enough to forestall possible problems.

As a result of this, researchers have begun to explore the possibilities of developing nontraditional antibiotic approaches for killing microorganisms. The goals of such development efforts include not only controlling antibiotic-untreatable infections, but in addition, limiting the development of additional antibiotic-resistant microbe strains by selecting a killing mechanism which does not involve the target's genetic material, or which is not otherwise mutagenic. This acts to prevent, at least in part, selection for or creation of strains potentially resistant to the action of the killing agent.

One such method being evaluated is the treatment of microbial infections by photodynamic therapy ("PDT"). This appears to be a valuable alternative method of eradicating bacteria, in part, because it appears to utilize a mechanism that is different from that typical of most antibiotics. Generally, PDT is based on the use of a photosensitizing molecule that, once activated by light, generates reactive oxygen species ("ROS") that are toxic to a large variety of prokaryotic and eukaryotic cells including bacteria, mycoplasma, and yeasts. Malik et al., *J. Photochem. Photobiol. B: Biol.*, 5:281–293 (1990); Bertolini et al., *Microbios*, 71:33–46 (1992).

One important feature of this approach is that the photosensitizing activity of many photodynamic agents is not impaired by bacterial resistance to antibiotics. Instead, it largely depends on the chemical structure of the photosensitizing agents themselves. Malik et al, *J. Photochem. Photobiol. B: Biol.*, 14:262–266 (1992). Various types of known neutral and anionic photosensitizers, for example, exhibit a pronounced phototoxic activity against Gram-positive bacteria while exhibiting no appreciable cytotoxic activity against Gram-negative bacteria unless the permeability of the outer membrane of the Gram-negative bacteria is altered by treatment with EDTA or polycations. Bertolini et al., *FEMS Microbiol. Lett.*, 71:149–156 (1990); Nitzan et al., *Photochem. Photobiol.*, 55:89–97 (1992). Without being limited to any one theory, it appears, in light of current research, that the more complex and thicker cellular envelope of Gram-negative bacteria (as compared to that of Gram-positive bacteria) may prevent the efficient binding of these photosensitizer molecules. In addition, the envelope may simply intercept and deactivate the cytotoxic reactive oxygen species generated by the photosensitizer molecules before fatal damage can be inflicted. Ehrenberg et al., *Photochem. Photobiol.*, 41:429–435 (1985); and Valduga et al., *Photochem. Photobiol. B: Biol.*, 21:81–86 (1993).

In contrast, positively charged photosensitizers, including porphyrins and phthalocyanines, promote the efficient inactivation of Gram-negative bacteria without the need of modifying the natural structure of the cellular envelope. Merchat et al., *J. Photochem. Photobiol. B: Biol.*, 32:158–163 (1996); and Minnock et al., *J. Photochem. Photobiol. B: Biol.*, 32:159–164 (1996). Again, without being limited to any one theory, it appears that the positive charge favors the binding of the photosensitizer molecule at critical cellular sites which, once damaged by exposure to light, cause the loss of cell viability. Merchat et al., *J. Photochem. Photobiol. B: Biol.*, 35:149–157 (1996).

One of the families of positively-charged photosensitizers currently being investigated is based on the porphyrin molecule. Porphyrins are macrocyclic molecular compounds with a ring-shaped tetrapyrrolic core. As such, porphyrins are commonly found in their dianionic form coordinated to a metal ion. The unique properties of the tetrapyrrolic core have made porphyrins central in many biological systems that play a vital role in many life processes. Several compounds which are critically important for essential biological processes, such as chlorophyll and heme, are derived from the coordination of a metal ion with a porphyrin nucleus. H. R. Mahler and E. H. Cordes, *Biological Chemistry*, 2d ed. 418, 1966.

Porphyrins are generally derived from the parent tetrapyrrole porphin by replacing hydrogens at one or more of the positions 1 and 8 as well as at one or more of the meso- (pyrrole bridging) carbon atoms with side chains such as, for example, methyls, ethyls, vinyls, propionic acids, or aromatic groups. Id. Porphyrins are often classified based on the side chains they contain. Hydrogenation of one or two pyrrole moieties generates the corresponding chlorophyll, and, respectively, bacteriochlorophyll derivatives.

As briefly noted above, porphyrins are able to form metal chelates with a large variety of metal ions, including: cobalt, copper, iron, magnesium, nickel, silver, and zinc. Id. at 419. Heme is an iron chelate of a porphyrin, while chlorophyll and bacteriochlorophyll are magnesium chelates. Porphyrins such as these are generally synthesized from the precursors glycine and succinyl CoA. See L. Stryer, *Biochemistry*, 2d ed. 504–507 (1981).

Present porphyrins and techniques for their use require that, in order to act as antimicrobial agents in the treatment of bacterial and other microbial infections, or even for use in the photosterilization of water, they must be employed in concentrations of at least 10 micromolar. They must then be irradiated for as long as about 30 minutes. See id.

One porphyrin-based cationic photosensitizer shown to be effective in killing both Gram-positive and Gram-negative bacteria, including the ability to efficiently inactivate *Escherichia coli*, is cationic meso-tetra(N-methyl-4-pyridyl) porphine, or "$T_4MPyP$". See Merchat, et al., *J. Photochem. & Photobiol. B: Biol.* 32:153–157, (1996); Merchat, et al., *J. Photochem. & Photobiol B: Biol.*, 35:149–157, (1996); Okuno, Synthesis, July 1980, 537, and Valduga et al., *Biochem. Biophys. Res. Comm.*, 256:84–88 (1999). Without being limited to any one theory, it appears that the phototoxic activity of this porphyrin is mediated by the impairment of enzymatic and transport functions of both the outer and cytoplasmic membrane. DNA was found not to be a primary target of $T_4MPyP$ photosensitization.

It has further been well established that the hydro- or lipo-philicity of a photosensitizer strongly affects the binding of the photosensitizer to a target cell, and as a consequence, its cytotoxic activity. Merchat et al., *J. Photochem. Photobiol. B: Biol.*, 35:149–157 (1996).

Currently known porphyrin photosensitizers, current methods of their synthesis, and known techniques for their use are inadequate for many intended applications. This is true in part due to the need for high concentrations of reagent and the requirement of extended irradiation periods. These factors render the methods burdensome and inconvenient. In addition, such conditions are not suitable for many medical and/or industrial applications.

It is thus seen that there is a need for novel photosensitizing antimicrobial agents for medical or other applications. It would be an improvement in the art to provide an antimicrobial agent that utilizes a pathway for inactivating or killing an organism which is non-mutagenic. It would be a further improvement in the art to provide alternate hydrophobic cationic porphyrin photosensitizers that are suitable for use against both Gram-positive and Gram-negative bacteria, as well as other microbes. Finally, it would be an additional improvement in the art to provide such a photosensitizer that is capable of functioning effectively at lower concentrations and over shorter periods than those currently known and taught in the art.

SUMMARY OF THE INVENTION

The compositions of matter of the present invention, the methods of their synthesis, and the associated methods for their use have been developed in response to the present state of the art. In particular, these aspects of the invention have been developed in response to the problems and needs in the art that have not yet been fully solved by currently available positively-charged porphyrins, porphyrin synthetic methods, and methods for the use of porphyrins to kill microbes including Gram-positive and Gram-negative bacteria. Thus, it is an overall objective of the present invention to provide positively-charged photodynamic porphyrins and methods for their use as photodynamic antimicrobial agents which perform better than those in the art.

To achieve the foregoing objects, and in accordance with the invention as embodied and broadly described herein in the preferred embodiment, a group of novel positively charged porphyrins is provided. Many of these novel porphyrins have up to four positive charges. In addition, these novel porphyrins also include at least one hydrophobic tail consisting of at least one hydrocarbon chain of between 6 and 22 carbons (inclusive) in length.

In one embodiment of the invention of the instant application, the photodynamic antimicrobial agent comprises a porphyrin having four quaternized nitrogens. In this form of the invention, the porphyrin further comprises a hydrocarbon tail beginning at one of the quaternized nitrogens. In some instances, the porphyrin is a light-absorbing reduced porphyrin. In some instances, the reduced porphyrin is selected from the group consisting of chlorin and bacteriochlorin. In other instances, the porphyrin or reduced porphyrin is a metal chelated porphyrin. In these instances, metals whose porphyrin chelates are useful as photodynamic antimicrobial agents include Mg (magnesium), Sc (scandium), Zn (zinc), Al (aluminum), In (indium), Tl (thallium), Si (silicon), Ge (germanium), Sn (tin), Pd (palladium), and Pt (platinum).

In other embodiments of the invention, the hydrocarbon tail is chosen from the group of straight chain alkyls, straight chain alkenes, branched alkyl chains, branched alkenyl chains, aromatics, mixed alkyl-aromatic species, and mixed alkenyl-aromatic species. In certain of these, the hydrocarbon tail contains between 6 and 22 carbons (inclusive). In others, the hydrocarbon tail contains between 10 and 18 carbons (inclusive). In some specific embodiments, the hydrocarbon tail comprises a benzyl group. In others, the hydrocarbon tail comprises a six-carbon chain. In yet others, the hydrocarbon tail comprises a ten-carbon chain. In other embodiments, the hydrocarbon tail comprises a fourteen-carbon chain. In still others, the hydrocarbon tail comprises an eighteen-carbon chain.

In other embodiments, the invention of the instant application is a photodynamic antimicrobial agent comprising a porphyrin having four quaternized nitrogens, and further comprising a hydrocarbon tail made up of between 6 and 22 carbons (inclusive), beginning at one of the quaternized nitrogens. In some of these embodiments, the hydrocarbon tail contains between 6 and 18 carbons. In others, the porphyrin is a light absorbing reduced porphyrin. In these, the reduced porphyrin may be selected from the group consisting of chlorin and bacteriochlorin. As above, the hydrocarbon tail is chosen from the group of straight chain alkyls, straight chain alkenes, branched alkyl chains, branched alkenyl chains, aromatics, mixed alkyl-aromatic species, and mixed alkenyl-aromatic species. In yet other embodiments, the porphyrin or reduced porphyrin is a metal chelated porphyrin. In these instances, metals whose porphyrin chelates are useful as photodynamic antimicrobial agents include Mg (magnesium), Sc (scandium), Zn (zinc), Al (aluminum), In (indium), Tl (thallium), Si (silicon), Ge (germanium), Sn (tin), Pd (palladium), and Pt (platinum).

In specific versions of the photodynamic antimicrobial agent of the instant invention, the hydrocarbon tail comprises a benzyl group. In others, the hydrocarbon tail comprises a six-carbon chain. In still others, the hydrocarbon tail comprises a ten-carbon chain. In others, the hydrocarbon tail comprises a fourteen-carbon chain. In still others, the hydrocarbon tail comprises an eighteen-carbon chain.

In a preferred embodiment, the invention comprises a series of derivatives of meso-tetra-(N-methyl-pyridyl) porphyrins, having four quaternized nitrogens, where one N-methyl group is replaced by a hydrocarbon tail ranging from C1 to C22. In some embodiments, the hydrocarbon tail contains between 6 and 22 carbons. In others, the hydrocarbon tail contains between 6 and 18 carbons.

In some of these meso-tetra-(N-methyl-pyridyl)porphyrin derivative embodiments, the porphyrin is a light absorbing reduced porphyrin. In some of these, the reduced porphyrin is selected from the group consisting of chlorin and bacteriochlorin. In others, the porphyrin or reduced porphyrin is a metal chelated porphyrin. In these instances, metals whose porphyrin chelates are useful as photodynamic antimicrobial agents include Mg (magnesium), Sc (scandium), Zn (zinc), Al (aluminum), In (indium), Tl (thallium), Si (silicon), Ge (germanium), Sn (tin), Pd (palladium), and Pt (platinum).

Further, in some of these meso-tetra-(N-methyl-pyridyl) porphyrin derivative embodiments, the hydrocarbon tail is chosen from the group of straight chain alkyls, straight chain alkenes, branched alkyl chains, branched alkenyl chains, aromatics, mixed alkyl-aromatic species, and mixed alkenyl-aromatic species. In some of these, the hydrocarbon tail comprises a benzyl group. In others, the hydrocarbon tail comprises a six-carbon chain. In others, the hydrocarbon tail comprises a ten-carbon chain. In still others, the hydrocarbon tail comprises a fourteen-carbon chain. In still others, the hydrocarbon tail comprises an eighteen-carbon chain.

In other embodiments of the invention, the invention comprises a method of synthesizing porphyrins with four symmetrically distributed positive charges on four quaternized nitrogens and a single hydrophobic hydrocarbon tail. An embodiment of this method of the invention comprises the steps of: providing a porphyrin, quaternizing a first nitrogen of the porphyrin by reacting it with a sub-stoichiometric quantity of a halide salt of the desired hydrophobic hydrocarbon tail, separating the mono-quaternized porphyrins from the non-mono-quaternized porphyrins, quaternizing the remaining nitrogens of the porphyrin using a methylating agent, and separating the resulting porphyrin with four symmetrically distributed positive charges and a single hydrophobic hydrocarbon tail from the reaction mixture. In some embodiments of the invention, either or both of the steps of separating the mono-quaternized porphyrins from the non-mono-quaternized porphyrins and separating the resulting porphyrin with four symmetrically distributed positive charges and a single hydrophobic tail are abridged, simplified, or even omitted when appropriate for a given application.

The halide salt may be selected from the group consisting of straight chain alkyls, straight chain alkenes, branched alkyls, branched alkenyls, aromatics, mixed alkyl-aromatics, and mixed alkenyl-aromatic halide salts. Additionally, the methylating agent may be methyl-p-toluene sulfomate, methyl iodide, dimethyl sulfate, methyl fluorosulfonate, and other suitable methylating agents. The step of separating the mono-quaternized porphyrin from the non-mono-quaternized porphyrins in the method of the instant invention may be accomplished utilizing solubility differences. Further, the step of separating the resulting porphyrin with four symmetrically distributed positive charges and a single hydrophobic tail may be accomplished using chromatography. This step may be simplified or omitted when the intended application of the porphyrins warrants, as in production of the porphyrins of the instant invention for industrial purposes, where high-percentages of purity are sufficient, and medical-grade purity is not required.

The invention further comprises methods of killing microbes including Gram-positive and/or Gram-negative bacteria utilizing photodynamic porphyrin antimicrobial agents. The term microbe is used herein to include microorganisms such as bacteria, fungi, algae, and viruses. Antimicrobial agents are a family of chemical agents which kill such microorganisms or suppress their growth. An embodiment of this method comprises the steps of providing a photodynamic antimicrobial agent comprising a porphyrin with four symmetrically-distributed positive charges and a hydrophobic tail, exposing Gram-positive and/or Gram-negative bacteria to said photodynamic antimicrobial agent, and irradiating the antimicrobial agent for a period of time.

In some versions of this method, the porphyrin used is a light absorbing reduced porphyrin. In these, the reduced porphyrin may be chosen from the group of chlorin and bacteriochlorin. In other versions, the porphyrin or reduced porphyrin is a metal chelated porphyrin. In these instances, metals whose porphyrin chelates are useful as photodynamic antimicrobial agents include Mg (magnesium), Sc (scandium), Zn (zinc), Al (aluminum), In (indium), Ti (thallium), Si (silicon), Ge (germanium), Sn (tin), Pd (palladium), and Pt (platinum).

In addition, in the embodiments of the instant invention, the hydrocarbon tail may be selected from the group consisting of straight chain alkyls, straight chain alkenes, branched alkyl chains, branched alkenyl chains, aromatics, mixed alkyl-aromatic species, and mixed alkenyl-aromatic species. In some of these, the hydrocarbon tail may contain between 6 and 22 carbons (inclusive). In others, the hydrocarbon tail may contain between 6 and 18 carbons (inclusive). In still others, the hydrocarbon tail may comprise a benzyl group. In others, the hydrocarbon tail may comprise a six-carbon chain. In still others, the hydrocarbon tail may comprise a ten-carbon chain. In others, the hydrocarbon tail may comprise a fourteen-carbon chain. Further, in other embodiments, the hydrocarbon tail may comprise an eighteen-carbon chain. In preferred embodiments of the invention, white light is used in the irradiation step of the method.

In some forms of this method, the porphyrin is present in a concentration of from about 10 $\mu$M to about 0.1 $\mu$M. In others, the porphyrin is present in a concentration of from about 5 $\mu$M to about 0.5 $\mu$M. In still other forms of the embodiment, the porphyrin is present in a concentration of 1 $\mu$M. In some forms of the embodiment, the period of time during which irradiation occurs may be from about 1 to about 10 minutes. In some embodiments of the invention, this period is about 5 minutes. The period of time for which irradiation is needed is determined based on the type of bacteria to be killed and the rate at which it takes up antimicrobial agent, the characteristics and concentration of the specific antimicrobial agent being used, the wavelength of the light to be used, and the intensity of the light to be used. One of skill in the art would be able to determine the period of time needed to kill or inactivate a given microbe based on these factors.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The presently preferred embodiments of the present invention will be best understood by reference to the figures and the following detailed description. It will be readily understood that the components of the compounds of the present invention, as generally described and illustrated in the figures herein, could be arranged and designed in a wide variety of different configurations. Further, the compounds may be used in a wide variety of concentrations, as evidenced herein. Thus, the following more detailed description of the embodiments of the apparatus, system, and method of the present invention, as represented in FIGS. 1 through 8, is not intended to limit the scope of the invention, as claimed, but is merely representative of presently preferred embodiments of the invention.

Porphyrins with four symmetrically-situated positive charges are made more active as photodynamic agents against Gram-positive and Gram-negative bacteria by including a hydrophobic "tail," comprising between 6 and 22 carbons (inclusive), which originates at one of the charged sites.

This increased photodynamic activity is most pronounced when the "tail" contained between 6 and 18 carbons (inclusive). One of skill in the art would expect similar results with comparable hydrophobic, straight-chain alkenyl, branched alkyl or alkenyl and aromatic or mixed alkyl-aromatic or alkenyl-aromatic tails.

The photophysical and photosensitizing effects of embodiments of the compounds of the instant invention have been evaluated. These studies confirm that cationic porphyrins represent a class of photosensitizing agents with an efficient antimicrobial activity. Specifically, flash photolysis data point out that the replacement of one N-methyl group in $T_4MPyP$ (a known photodynamic sensitizer) with progressively longer hydrocarbon chains has only a minor influence on the quantum yield and lifetime of the lowest triplet state. This further shows only minor influence on the efficiency of photosensitized oxidation of a model biological substrate, such as N-acetyl-L-tryptophanamide ("NATA") (see Hydrophobicity Example 11, Table 4).

Without being limited to any one theory, it appears that highly hydrophobic porphyrins in neutral and homogeneous aqueous medium generate large oligomers which are undetectable by the conventional time-resolved spectroscopic techniques owing to their short lifetime.

On the other hand, the presence of up to 30% dimeric species in the overall population of porphyrin molecules, as suggested by the fluorescence decay studies with $T_4MPyP$ (Hydrophobicity Example 9, Table 2), appears to have no appreciable effect on the efficiency of triplet generation and NATA photooxidation.

The presence of aggregated moieties can also control the efficiency of the antimicrobial phototoxic action of porphyrins, as shown by the smaller inhibition of *E. coli* growth caused by irradiation in the presence of 1 μM C22 as compared with the extensively monomeric C10, C14 and C18 derivatives. However, a predominant role in this case is certainly played by the affinity of the various porphyrins towards bacterial cells. Thus, $T_4MPyP$ and its C6 analogue, which exhibit a relatively lower binding to both *S. aureus* and *E. coli* cells (see FIGS. 6 and 7), photoinduce a significant bacteriostatic and bactericidal action against both cell strains only at concentrations as high as 10 μM, whereas the C10, C14, and C18 analogues cause similar effects at a ten-fold lower concentration. These results would suggest that a limited increase in the hydrophobicity of the photosensitizer molecule enhances its affinity for bacterial cells, hence promoting a more efficient photoinactivation.

In the instant invention, the degree of hydrophobicity has been modulated by the introduction of a saturated alkyl chain of controlled length. Without being limited to any one theory, it appears likely that such a chain brings about an additional effect, including the possibility that its presence interferes with the normal functions and/or morphology of bacterial cells, as shown by the dark toxicity displayed by the longer chain porphyrin derivatives. Recent findings further demonstrate that the covalent attachment of a polylysine chain to the photosensitizer molecule potentiates its activity against a variety of microbial strains. Similar results were reported by Hamblin using polylysine-derivatized chlorin e6.

In the instant invention, the presence of a lipophilic substituent should facilitate the localization of the porphyrin photosensitizer in the membranous cell domain. As a consequence, there is a reduced probability of involving the genetic material in the photoprocess, hence of promoting the onset of mutagenic effects. At the same time, a high porphyrin concentration in the membrane should optimize the photoinactivating activity against antibiotic-resistant bacteria since this phenomenon is most often related with the expression of specific membrane proteins. The high photosensitivity displayed by the methicillin-resistant *S. aureus* strain to the irradiation in the presence of the C10–C14 derivatives fully supports this hypothesis.

The porphyrins of the instant invention showed photodynamic effects against Gram-positive and Gram-negative bacteria at between 5- and 20-fold lower concentrations of the porphyrin sensitizer than the concentrations used in Merchat. The porphyrin with the benzyl tail was about twice as effective as the base porphyrin under the same conditions. Without being limited to any one theory, it appears that the hydrocarbon moiety may enhance the affinity of the porphyrin for the cytoplasmic membrane of the bacterial cells, thus inducing a greater accumulation and a tighter binding. In addition to this, it may cause a limited but significant disorganization of the native architecture of the membrane, thereby increasing the degree of cell photosensitivity.

Thus, an embodiment of the invention comprises a porphyrin or light absorbing reduced porphyrin (such as chlorin or bacteriochlorin) and its photodynamically-active metal chelate with four symmetrically-distributed positive charges (quaternized nitrogens) and at least one hydrophobic hydrocarbon tail beginning at one of the quaternized nitrogens, said tail containing between 6 and 22 carbons inclusive. Several examples of such porphyrins are: 5-(4-N-decylpyridyl)-10,15,20-tris (4-N-methylpyridyl) porphine tetra chloride salt or other suitable anions and salt forms such as the dihydrochlorides, or their 5, 10, 15, 20 tetra(3-pyridyl)porphine analogues, and 5-(4-N-tetradecyl dimethyl aminophenyl)-10,15,20-tris (4-N-trimethyl aminophenyl) porphine tetra chloride salt or other suitable anions and salt forms such as the dihydrochlorides.

1. General Synthetic Procedure

The photodynamic antimicrobial porphyrins of the instant invention are prepared according to the following generic synthetic method. Specific synthesis examples follow this generic description, but should not be construed to limit the scope of the broad general method of the instant invention. The porphyrins described in this application are prepared from the known porphyrins containing four nitrogens bonded to groups distributed symmetrically around the porphyrin nucleus. These nitrogens may be converted to quaternized ammonium salts bearing a positive charge.

In a first step of this invention, one of these nitrogens is converted to the quaternized form by allowing the porphyrin to react with a sub-stoichiometric quantity of alkyl, alkenyl, or benzyl halide in a suitable solvent. The resulting monoquaternized porphyrin is then separated from the starting porphyrin by employing solubility differences. This step may be simplified, abridged, or omitted when the intended application of the product porphyrins warrants.

The monoquaternized porphyrin is then completely quaternized at the remaining nitrogen positions by using a methylating agent such as methyl-p-toluene sulfonate, dimethyl sulfate, methyl fluorosulfonate, methyl iodide, or other commonly used suitable methylating agents.

The final product is purified by removing it from the reaction mixture using a separation technique such as chromatography. The counter ions (anions) can be changed using ion exchange medium. This final separation step may also be simplified, abridged, or omitted when the intended application of the product porphyrins so warrants.

2. Synthetic Examples

Example 1

Preparation of 5-(4-N-decylpyridyl)-10,15,20-tris(4-N-methylpyridyl)-21H,23H-porphine tetrachloride dihydrochloride salt:

1 gram (1.61 mmoles) of 5, 10, 15, 20 tetra(4-pyridyl)-21H,23H-porphine plus 285 mg (1.29 mmoles) of 1-bromodecane were refluxed for 22 hours in 20 ml of glacial acetic acid. Thin layer chromatography on C-18 silica reversed phase plate eluting with 90/10 methanol/6N HCl V/V showed approximately 35–40% mono-N-decyl derivative with slightly more starting porphyrin and trace of the di-N-decyl derivative (decreasing Rf with increasing substitution). The mixture was poured into 200 ml of methanol and cooled for several hours in the refrigerator, then for several hours in the freezer to precipitate the starting porphyrin. The precipitate was collected by centrifugation, and the decanted solvent containing the product was dried on the rotary vacuum. The resulting solid was refluxed in 150 ml of methanol for 4 hours, cooled overnight in the refrigerator, and the resulting solid was removed by centrifugation. Thin-layer chromatography of the decanted solution (same system as above) showed predominantly monosubstituted product, with some disubstituted porphyrin, and a trace of starting porphyrin. The solvent was removed by rotary evaporation, and then used for the next step without further purification.

The solid was dissolved in 50 ml of N,N dimethylformamide containing 1 gram of methyl-p-toluenesulfonate, and refluxed for 2 hours. The solvent was removed by rotary evaporation, and the solid dissolved in 50 ml of deionized water and filtered to remove insolubles. The solution was applied to an 8 cm×2 cm chromatography column packed with 40 micron Butyl(C-4) reversed phase packing (J. T. Baker). The column was washed briefly with 3 N HCl, then eluted with 50% methanol, 50% 1 N HCl. The main band was collected and dried by rotary evaporation to yield 400 mg of the shiny dark green powder which was estimated to be greater than 95% by thin layer chromatography on Whatman KC2 silica reversed phase plates eluting with 50% methanol, 50% 1 N HCl V/V Rf 0.2.

Example 2

Preparation of 5-(4-N-tetradecylpyridyl)-10,15,20-tris(4-N-methylpyridyl)-21H,23H-porphine tetrachloride dihydrochloride salt:

1 gram (1.61 mmoles) of 5, 10, 15, 20 tetra(4-pyridyl)-21H,23H-porphine plus 357 mg (1.29 mmoles) 1-bromotetradecane along with 500 mg of anhydrous sodium acetate were refluxed for 16 hours in 20 ml of glacial acetic acid. Thin layer chromatography on silica plates eluting with isopropanol/water/acetone/acetic acid/concentrated ammonium hydroxide, V/V/V/V/V showed about 30% monosubstituted porphyrin with traces of disubstituted and remainder starting porphyrin. The solvent was removed by rotary evaporation, and the solid was extracted by refluxing for 4 hours with 200 ml of methanol. This was filtered while hot to remove most of the starting porphyrin, then again after cooling in the refrigerator for several hours to remove most of the remaining starting porphyrin. The solution was reduced in volume on the rotary evaporator to about 20 ml, then cooled in the refrigerator for several hours. The solid filtered off on a small Buchner funnel contained mostly mono-substituted porphyrin with some starting porphyrin, as ascertained by the above thin-layer chromatography system.

The solid was refluxed in 25 ml of N,N dimethylformamide containing 0.5 g methyl-p-toluene sulfonate for 2 hours. The solvent was removed by rotary evaporation, and the solid was dissolved in 50 ml of deionized water, filtered to remove insolubles, and applied to an 8 cm×2 cm chromatography column packed with 40 micron Butyl(C-4) reversed phase packing (J. T. Baker). The column was washed briefly with 3 N HCl, then eluted with 50% methanol, 50% 1 N HCl, V/V. The heart of the main band was collected and dried by rotary evaporation to yield 110 mg of a shiny dark green powder which was estimated to be greater than 95% by thin-layer chromatography on Whatman KC2 silica reversed phase plates eluting with 70% methanol, 30% 1 N HCL V/V Rf=0.22. A further 80 mg of product was recovered from other fractions of the eluent with a purity of approximately 90%.

Example 3

Preparation of 5-(4-N-hexylpyridyl)-10,15,20-tris(4-N-methylpyridyl)-21H,23H-porphine tetrachloride dihydrochloride salt:

1 gram (1.61 mmoles) of 5, 10, 15, 20 tetra(4-pyridyl)-21H,23H-porphine plus 273 mg (1.29 mmoles) of 1-iodohexane and 500 mg of anhydrous sodium acetate were refluxed for 18 hours in 20 ml of glacial acetic acid. Thin layer chromatography on silica plates eluting with isopropanol/water/acetone/acetic acid/concentrated ammonium hydroxide, V/V/V/V/V showed only 15–20% of the monosubstituted product. 144 mg more 1-iodohexane was added to the mixture, and reflux continued for an additional 10.5 hours. Thin layer chromatography with above system showed 20–25% monosubstituted product. A further 144 mg of 1-iodohexane was added to the mixture and reflux continued for an additional 12 hours resulting in an estimated 30% monosubstituted product by above thin layer chromatography system. The solvent was removed by rotary evaporation, and the solid was extracted for 2 hours with 100 ml of refluxing methanol. The mixture was cooled in the refrigerator for 24 hours then filtered to remove most of the starting porphyrin. The volume was reduced on the rotary evaporator to approximately 30 ml and cooled overnight in the refrigerator. Filtration yielded about 100 mg of solid which contained approximately 85 to 90% of the monosubstituted porphyrin estimated by the thin layer system described above.

The solid was refluxed along with 400 mg of methyl-p-toluene sulfonate in 20 ml of N,N dimethylformamide for 2 hours, then the solvent removed by rotary evaporation. The solid was dissolved in 30 ml of hot water, filtered, and applied to an 8 cm×2 cm chromatography column packed with 40 micron Butyl(C-4) reversed phase packing (J. T. Baker). The column was washed briefly with 3 N HCl, then eluted with 70% 1N HCl, 30% methanol, V/V. Three fractions were collected and evaluated by thin layer chromatography on Whatman KC2 silica reversed phase plates eluting with 50% methanol, 50% 1 N HCl, V/V. The first fraction contained the desired product contaminated with about 20% of the tetra N-methylated starting porphyrin. The second fraction contained the desired product with a purity estimated at 95% or better, and the third fraction was predominantly the di-N-hexyl, di-N-methyl substituted porphyrin. The solvent was removed from the second fraction on the rotary evaporator, and the solid was dissolved in a few ml of water, titrated with a few drops of 3 N HCl until the solution turned dark green, following which it was frozen and dried on the lyophilizer. Yield of the shiny dark green powder was 45 mg. Rf=0.36 in the reversed phase thin layer system described above.

Example 4

Preparation of 5-(4-N-octadecylpyridyl)-10,15,20-tris(4-N-methylpyridyl)-21H,23H-porphine tetrachloride dihydrochloride salt.

1 gram (1.61 mmoles) of 5, 10, 15, 20 tetra(4-pyridyl)-21H,23H-porphine plus 490 mg(1.29 mmoles) 1-iodo-octadecane were refluxed for 16 hours in 20 ml of glacial acetic acid. Thin-layer chromatography on C-18 silica reversed phase plate eluting with 90/10 methanol/6N HCl V/V showed approximately equal amounts of the mono-N-octadecyl derivative and starting material with a trace of the di-N-octadecyl derivative (decreasing Rf with increasing substitution). The solvent was removed by rotary evaporation and 200 ml of methanol plus 1 ml of glacial acetic acid was added and the solution refluxed for 6 hours, then allowed to stand at room temperature overnight. The solution was filtered, and the filtrate, which contained mostly mono-substituted porphyrin with small amounts of di-substituted and starting porphyrin, was evaporated to dryness on the rotary evaporator. The solid was refluxed for 3 hours in 100 ml of methanol, allowed to stand at room temperature overnight, then placed in the freezer briefly, filtered, and the filtrate added to the previous filtrate and evaporated to dryness as before.

The dried combined filtrates were dissolved in 75 ml of N,N dimethylformamide containing 1.5 grams of methyl-p-toluene sulfonate and refluxed for 2 hours. The solvent was removed on the rotary evaporator and the solid dissolved in 75 ml of hot deionized water and filtered to remove insolubles. The solution was applied to a 2 cm×10 cm chromatography column packed with 40 micron Butyl(C-4) reversed phase packing (J. T. Baker). The column was first eluted with 3 N HCl, then 50/50 V/V methanol/1N HCl to remove some impurities. The product (estimated at greater than 95% by thin layer chromatography on Whatman KC2 Silica reversed phase plates, eluting with 70/30 methanol/3 N HCl V/V Rf 0.25) was eluted off the column with 70% methanol, 30% 3N HCL V/V, and dried on the rotary evaporator to yield 400 mg of the shiny dark green powder.

Example 5

Preparation of 5-(4-N-docosanyl)-10,15,20-tris(4-N-methylpyridyl)-21H,23H-porphine tetrachloride dihydrochloride salt.

1 gram (1.61 mmoles) of 5, 10, 15, 20 tetra(4-pyridyl)-21H,23H-porphine plus 502 mg (1.29 mmoles) of 1-bromodocosane along with 500 mg of anhydrous sodium acetate were refluxed for 16 hours in 20 ml of glacial acetic acid. 200 mg more 1-bromodocosane was then added, and the solution refluxed for a further 8 hours. The solution was then taken to dryness on the rotary evaporator. The mono-substituted derivative could not be separated from the starting porphyrin either by fractional crystallization or by column chromatography on silica. Therefore, the crude reaction mixture was refluxed with 1 gram of methyl-p-toluene sulfonate in 50 ml of N,N dimethylformamide to complete the quaternization process. The solution was poured slowly into 125 ml of rapidly stirring water, filtered, and applied to an 8 cm×2 cm chromatography column packed with 40 micron Butyl(C-4) reversed phase packing (J. T. Baker). The column was washed briefly with 1 N HCl, then eluted with 40% methanol, 60% 1 N HCl, V/V, then 60% methanol, 40% 1 N HCl, V/V to remove tetra N-methylated porphyrin. The product was eluted from the column with 80% methanol, 20% 1 N HCl, V/V, and the solvent removed by rotary evaporation. The product was dissolved in a little water, a few drops of 1 N HCl added until it turned dark green, and then frozen and dried on the lyophilizer, yielding 180 mg of shiny dark green powder. Thin layer chromatography on Whatman KC2 silica reversed phase plates eluting with 70% methanol, 30% 3 N HCl, V/V, shows a purity of approximately 95% with an Rf=0.18.

Example 6

Preparation of 5-(4-N-benzylpyridyl)-10,15,20-tris(4-N-methylpyridyl)-21H,23H-porphine tetrachloride dihydrochloride salt.

1 gram (1.61 mmoles) of 5, 10, 15, 20 tetra(4-pyridyl)-21H,23H-porphine plus 193 mg (1.13 mmoles) of benzyl bromide along with 500 mg of anhydrous sodium acetate, were refluxed in 20 ml of glacial acetic acid for 2 hours. Thin layer chromatography on silica plates eluting with isopropanol/water/acetone/acetic acid/concentrated ammonium hydroxide, V/V/V/V/V showed approximately 50% of the mono-N-benzyl derivative with substantial amounts of starting porphyrin and the di-N-benzyl derivatives. The solution was poured into 150 ml of methanol while still hot and cooled in the refrigerator overnight. The solution was filtered to remove most of the starting porphyrin, then taken to dryness on the rotary evaporator.

The solid containing the mono-N-benzyl porphyrin derivative was refluxed along with 500 mg of methyl-p-toluene sulfonate in 25 ml of N,N dimethylformamide for 2 hours, then the solvent removed by rotary evaporation. The solid was dissolved in 50 ml of hot water, filtered, and applied to an 8 cm×2 cm chromatography column packed with 40 micron Butyl (C-4) reversed phase packing (J. T. Baker). The column was washed briefly with 3 N HCl, then eluted with from 20 to 50% methanol in 1 N HCl, V/V. The main band eluted contained the desired product, and the solvent was removed by rotary evaporation to yield 255 mg of shiny dark green powder. Estimated purity by thin layer chromatography on Whatman KC2 silica reversed phase plates eluting with 70% methanol, 30% 1 N HCl, V/V was greater than 95% Rf=0.33.

Example 7

A series of novel positively-charged porphyrins was prepared and tested against *Escherichia coli* (a Gram-negative bacterium) and antibiotic-resistant *Staphylococcus aureus* (a Gram-positive bacterium). It was determined that porphyrins with four symmetrically-situated positive charges were made much more active as photodynamic agents against these bacteria by inclusion of a hydrophobic "tail" containing between 6 and 22 carbons (inclusive), originating at one of the charged sites. Furthermore, this increased photodynamic activity was most pronounced when the "tail" contained greater than 6 and less than 18 carbons. Only straight-chain alkyl tails and a benzyl tail were prepared and tested, but one of skill in the art would expect similar results with comparable hydrophobic, straight-chain alkenyl, branched alkyl or alkenyl and aromatic or mixed alkyl-aromatic or alkenyl-aromatic tails. The above-mentioned porphyrins showed photodynamic effects comparable to the base porphyrin ($T_4MPyP$) used in the Merchat references cited above against these bacteria at between 5- and 20-fold lower concentrations of the porphyrin sensitizer. The porphyrin with the benzyl tail was about twice as effective as the base porphyrin under the same conditions. See Table 1.

The bacteria were grown aerobically at 20° C. in brain heart infusion broth (Difco) with added 1.5% NaCl. *Escherichia coli* cells were grown aerobically at 37° C. in brain heart infusion broth. Cells in the logarithmic phase of growth were harvested by centrifugation and washed three times with 10 mM phosphate-buffered saline solution at 7.4 pH, which also had 2.7 mM KCl and 0.14 M NaCl. The cells were diluted in this buffer to a final concentration of about 107 cells/ml.

Example 8

The abilities of various examples of the porphyrins of the instant invention to kill Gram-negative and Gram-positive bacteria were tested against that of $T_4MPyP$. See Table 7.

Each of the compounds was incubated with *E. coli* and *S. aureus* cells for 5 minutes, following which the samples were irradiated with white light for varying lengths of time.

TABLE 7

Growth inhibition (%) of *E. coli* and *S. aureus* cells incubated for 5 minutes with T4MPYP and different mono-derivatives and irradiated with white light.

| Sens. | Concentration ($\mu$M) | Irradiation time (min.) | Growth inhibition (%) E. coli | S. aureus |
|---|---|---|---|---|
| T4MPYP | 10 | 5 | 28.7 | 96.4 |
|  |  | 15 | 82.8 | 100 |
| mono-C6 | 0.5 | 5 | 4.8 | — |
|  |  | 30 | 15.5 | — |
|  | 10 | 5 | 98.7 | — |
|  |  | 10 | 100 | — |
| mono-C10 | 0.5 | 5 | 46.3 | 73.9 |
|  |  | 10 | 92 | 87.9 |
|  | 1 | 5 | 96.1 | — |
|  |  | 10 | 100 | — |
| mono-C14 | 0.5 | 5 | 81.8 | 72.7 |
|  |  | 10 | 100 | 88.9 |
| mono-C18 | 0.1 | 5 | — | 12.7 |
|  |  | 10 | — | 20.2 |
|  | 0.5 | 5 | 26 | 41.4 |
|  |  | 10 | 56.6 | 58.1 |
|  | 1 | 5 | 57.9 | — |
|  |  | 10 | 95.7 | — |
| mono-C22 | 1 | 5 | 2.7 | 69.7 |
|  |  | 10 | — | 90.2 |
|  |  | 30 | 18.5 | — |
| mono-benzyl | 10 | 5 | 54.1 | — |
|  |  | 10 | 100 | — |

$T_4MPyP$ was first exposed to *E. coli* and *S. aureus* at a concentration of 10 $\mu$M for 5 minutes. A first sample was irradiated for 5 minutes. This resulted in a growth inhibition of 28.7% for *E. coli*, and 96.4% for *S. aureus*. A second sample was irradiated for 15 minutes, resulting in growth inhibition of 82.8% of *E. coli*, and 100% for *S. aureus*.

A mono-substituted porphyrin was next exposed to *E. coli* and *S. aureus*. This porphyrin was substituted with a hexane tail. A first sample was exposed to the bacteria at a concentration of 0.5 $\mu$M for 5 minutes. At 5 minutes, *E. coli* was only inhibited 4.8%. At 30 minutes, *E. coli* was 15.5% inhibited. A second sample was exposed to 10 $\mu$M mono-substituted porphyrin, and at 5 minutes, *E. coli* was 98.7% inhibited. At 10 minutes, the *E. coli* was 100% inhibited.

*E. coli* and *S. aureus* were next treated with a second mono-substituted porphyrin, this one with a ten-carbon tail, again for 5 minutes. A first sample was treated with 0.5 $\mu$M porphyrin and irradiated for 5 minutes. At 5 minutes, *E. coli* was inhibited in growth by 46.3%, while *S. aureus* was inhibited by 73.9%. At 10 minutes, the *E. coli* was 92% inhibited, while the *S. aureus* was inhibited by 87.9%.

A second sample was treated with the ten-carbon substituted porphyrin at a concentration of 1 $\mu$M. After 5 minutes of irradiation with white light, the *E. coli* was inhibited by 96.1%, and at 10 minutes, the *E. coli* was inhibited 100%.

The combined investigations of the photophysical and photobiological properties of the porphyrins of the instant invention proved to be useful in understanding the mechanism by which these cationic porphyrins induce antimicrobial activity. Without being limited to any one theory, the photophysical data appeared to show that in buffered water, radiative deactivation plays a modest role. Intersystem crossing to the triplet manifold, however, appears to be the most important relaxation pathway of the S1 state of these porphyrins, with the exception of the longer chain compound C22, where the relaxation mainly occurs by internal conversion to the ground state, owing to its substantial aggregation in water.

Without being limited to any one theory, it thus appears that the triplet state is largely responsible for the photosensitizing properties of the porphyrins. The T1 properties, and in particular the lifetime of T1, are largely influenced by the formation of aggregated species. This, in turn, correlates with a drop in photosensitizing activity.

It thus appears important to counterbalance the tendency of the tetrapyrrolic macrocycle to undergo aggregation in aqueous media by attaching carefully designed peripheral substituents. The data obtained in the research conducted by the applicants suggests that this goal can be achieved in a preferred embodiment of the invention by the addition of one hydrocarbon chain of appropriate size (C10–C14) to the porphyrins. This addition yields the further advantage of enhancing the affinity of the porphyrin for bacterial cells.

The need for the introduction of structural elements that increase the efficiency of the photosensitizing action is especially important in the case of Gram-negative bacteria. It has been repeatedly reported that these bacteria are markedly less susceptible to photosensitized inactivation than the Gram-positive bacteria. Malik et al., *J. Photochem. Photobiol. B: Biol.*, 5:281–293 (1990). The findings contained in the instant application further support this conclusion. See Hydrophobicity Example 13, Table 5.

The engineering of photosensitizer molecules to develop a concerted dark- and phototoxicity appears to be preferable, especially for in vivo phototherapeutic applications, to current methods. Many of these current methods are based on the parallel introduction of two sets of chemicals. Members of the first set of chemicals act to render the bacterial wall more permeable. Such chemicals often include polymixin nonapeptide or EDTA. Malik et al., *J. Photochem. Photobiol. B: Biol.*, 14:262–266 (1992), Bertoloni et al., *FEMS Microbiol. Lett.*, 71:149–156 (1990). The second set of chemicals includes photosensitizers which are better able to function after the bacteria have been rendered more permeable.

Figure 1:
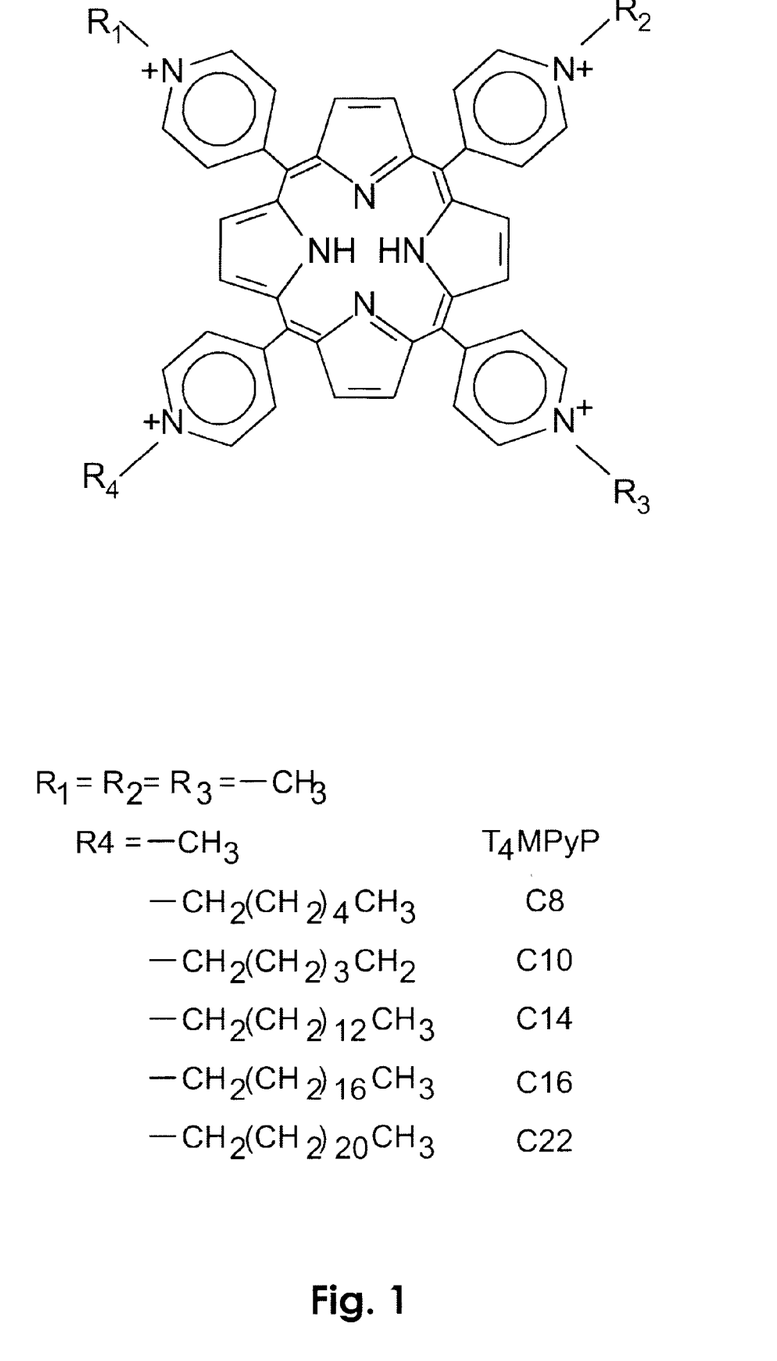
FIG. 1 is an illustration of the chemical structure of the known photodynamic antimicrobial agent T$_4$MPyP and the novel T$_4$MPyP derivatives of the instant invention bearing an N-alkyl substituent with an increasing number of carbon atoms.
Figure 2:
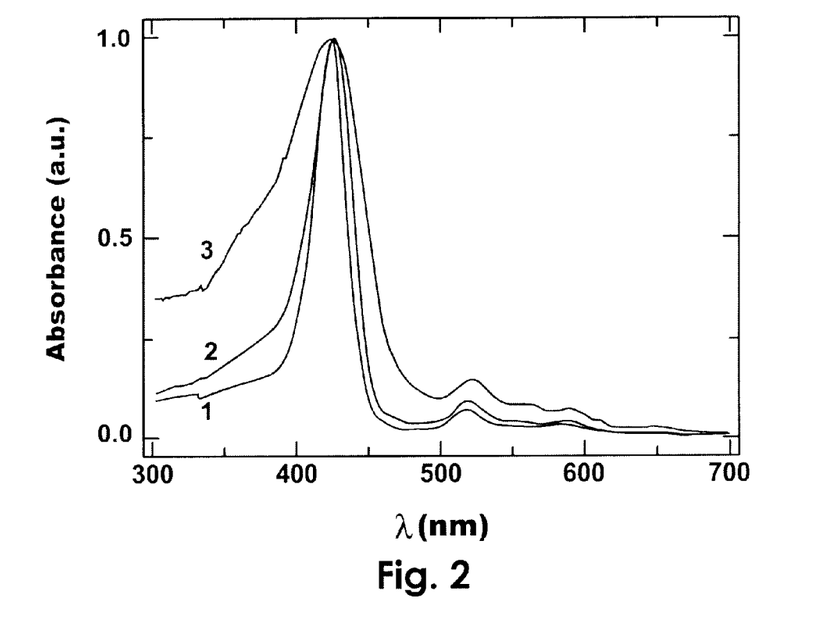
FIG. 2 is a graph showing the normalized absorption spectra of $T_4MPyP$ (1), the C18 derivative (2), and the C22 derivative (3) in phosphate buffered solution at pH 7.4.

3. Materials and Methods for Assessing the Effect of Increasing Hydrophobicity on Affinity for Bacteria and Measuring Photophysical Properties Porphyrins and Other Chemicals:

Meso-tetra(N-methyl-4-pyridyl)porphine tetratosylate ($T_4MPyP$) was purchased from Frontier Scientific (Logan, Utah, USA) and used without further purification. The various meso-substituted porphines, in which one N-methyl group of $T_4MPyP$ was replaced by an alkyl chain, each with an increasing number of carbon atoms, were synthesized in the Frontier Scientific (Logan, Utah, USA) laboratories. The chemical structures of the various porphyrin derivatives are shown in FIG. 1. All other chemicals were analytical grade reagents and were used without further purification.

Spectroscopic and Photophysical Studies:

Ground-state absorption spectra of the porphyrins (ca. 5 $\mu$M in phosphate buffered saline (PBS, pH=7.4) were recorded with a Lambda 5 Perkin-Elmer spectrophotometer. Fluorescence spectra, corrected for the instrumental response, were recorded with a Perkin-Elmer (model LS) or a Spex (Fluorolog F112) spectrofluorimeter. Fluorescence quantum yields ((IF) of the porphyrin derivatives in PBS and in water containing 2% sodium dodecylsulfate (a detergent, hereinafter "SDS") were determined by measuring the area of the emission spectrum (600–800 nm range, excitation at 560 nm) and using tetra-n-propylporphycene in toluene as a reference ($\Phi_F$=0.38). Braslavsky et al, *J. Photochem. Photobiol. B: Biol.*, 40:191–198 (1997). In all cases, the absorbance of the sample and the reference solution were kept below 0.1 at the excitation wavelength to minimize inner filter effects.

Fluorescence decay times of the porphyrin samples were measured by means of a Spex Fluorolog-τ2 spectrofluorimeter based on the phase-shift method. The frequency response curves (phase-shift and demodulation ratio vs. frequency) were globally analyzed.

Laser flash photolysis experiments were carried out by use of the setup previously described in Gomer, et al., with excitation wavelengths of 355 and 420 nm. Gorner, et al., Photoinduced electron transfer between styrylanthracenes and electron donors and acceptors in acetonitrile, *J. Chem. Soc. Faraday Trans.*, vol. 88, pp. 29–34 (1992).

Photostability Studies:

The photostability of the porphyrins was determined in PBS upon illumination of 11M solutions with white light (400–800 nm) isolated from the emission of a quartz-halogen lamp equipped with UV and infrared filters (Teclas, Lugano, Switzerland). The lamp was operated at a fluence rate of 150 mW/cm². During irradiation, the solution was magnetically stirred and kept at 37° C. The concentration of the porphyrin samples was monitored spectrophotometrically at different irradiation times and the photostability was expressed as the percent residual absorbance referred to the absorbance measured prior to irradiation.

Photooxidation Studies in vitro:

The photosensitizing activity of the various porphyrins was tested by measuring their efficiency in promoting the photooxidation of N-acetyl-L-tryptophanamide (NATA, Aldrich Chem. Co.) as a model biological substrate. Toward this aim, 10 $\mu$M NATA in PBS or in water containing 2% SDS was irradiated in the presence of 5 $\mu$M porphyrin. The irradiations were performed with 515±10 nm-light isolated by means of an interference filter (Balzers, Liechtenstein), while the solution (2 ml) was magnetically stirred in a quartz cuvette of 1-cm optical path and kept at 25° C. The photosensitized modification of NATA was followed by measuring the decrease in the intensity of its fluorescence emission spectrum (300–450 nm) upon excitation with 290 nm-light at various irradiation times. Plots of in F°/F (where F° and F represent the fluorescence intensity at time 0 and t, respectively) vs. the irradiation time allowed the first-order rate constants of the photo-process to be derived.

The intensity of the incident light was measured by using Aberchrome 999P in toluene as an actinometer. Heller, *EPA Newslett.*, 29:49–60 (1987). This parameter was used to calculate the quantum yields of NATA photooxidation sensitized by the different porphyrins.

Binding of Porphyrins to Bacteria Cells:

*Escherichia coli* strain O4 (wild type), and methycillin-resistant *Staphylococcus aureus*, strain MRSA 110, were grown aerobically at 37° C. in brain heart infusion broth (BHI, Difco, Detroit, Mich.). The cells in the stationary phase of growth were harvested by centrifugation (2,000 g for 15 min) of the broth cultures, washed twice with 10 mM PBS at pH=7.4, containing 2.7 mM KCl and 0.14 M NaCl, and suspended in PBS at a density of 108–109 cells/ml (absorbance of about 0.7 at 650 nm). Aliquots of 5 ml of the cell suspension were incubated with 1 $\mu$M porphyrins for 5 min in the dark at room temperature. After incubation the suspensions were centrifuged and the cell pellets were collected immediately or washed with PBS and centrifuged again for one or three times.

The amount of cell-bound porphyrins was determined in the pellets after resuspension and overnight-incubation in 2% aqueous SDS. The porphyrin concentration in the cell lysate was determined by measuring the intensity of red fluorescence (600–750 nm) emitted after excitation at 420 nm and interpolating the data on a calibration plot obtained with known porphyrin concentrations. The protein content of the cell samples was determined by the method of Lowry (Lowry et al., *J. Biol. Chem.*, 193:265–275 (1951)) and was used to express the amount of porphyrin bound to the cells as nanomoles of porphyrin/mg of protein.

Dark- and Photo-Toxicity of Porphyrins on Bacteria Cells:

The toxic effects of $T_4MPyP$ and its analogues on *E. coli* and *S. aureus* cells were evaluated by measuring the extent of growth inhibition (bacteriostatic effect) and reduction of survival (cytocidal/bacteriocidal effect) following treatment with porphyrin in the dark or upon light exposure.

In all cases, 5 ml of the cell suspension (108–109 cells/ml) were incubated for 5 min in the dark at room temperature with the selected photosensitizer at concentrations ranging between 0.5 and 10 $\mu$M. After dark-incubation, some of the cell samples were irradiated with white light (150 mW/cm$^2$). During irradiation, (up to 30 min) the cells were kept at 37° C. and magnetically stirred. The treated and untreated control cells were diluted with BHI and maintained at 37° C. while the absorbance of the suspension at 650 nm was monitored at predetermined time periods for determining growth curves. The percent of growth inhibition in the treated cells was calculated by the following equation:

$$[1-(A_X-A_0)/(A_C-A_0)]\times 100$$

where $A_X$, and $A_C$ are the absorbances measured after 3 h incubation, respectively, for the treated and control cell suspensions, respectively, while $A_0$ represents the initial absorbance and the $A_C$ is that of the control cell suspension after 5 hours incubation. Cell survival was determined by plating serially diluted aliquots of treated and untreated cells on brain heart agar and counting the number of colonies after 18–24 h incubation at 37° C.

4. Hydrophobicity Examples

Example 9

Absorption and Emission Properties

The ground state absorption spectrum of $T_4MPyP$ (see FIG. 2) showed an intense Soret band at 422 nm with a molar absorption coefficient of 194,000 M$^{-1}$ cm$^{-1}$, typical of meso-substituted free-base porphyrins, and the Q-bands at 520, 552, 585 and 640 nm. Generally, an increase in the size of the alkyl tail at one pyrrole nitrogen did not affect the ground state spectrum of the porphyrins. A marked change was observed only for the C22-derivative (see FIG. 2). In particular, a ca. 4400 cm$^{-1}$ broadening was detected in the region of the Soret-band, which indicates an extensive aggregation of this porphyrin sample.

Figure 3:
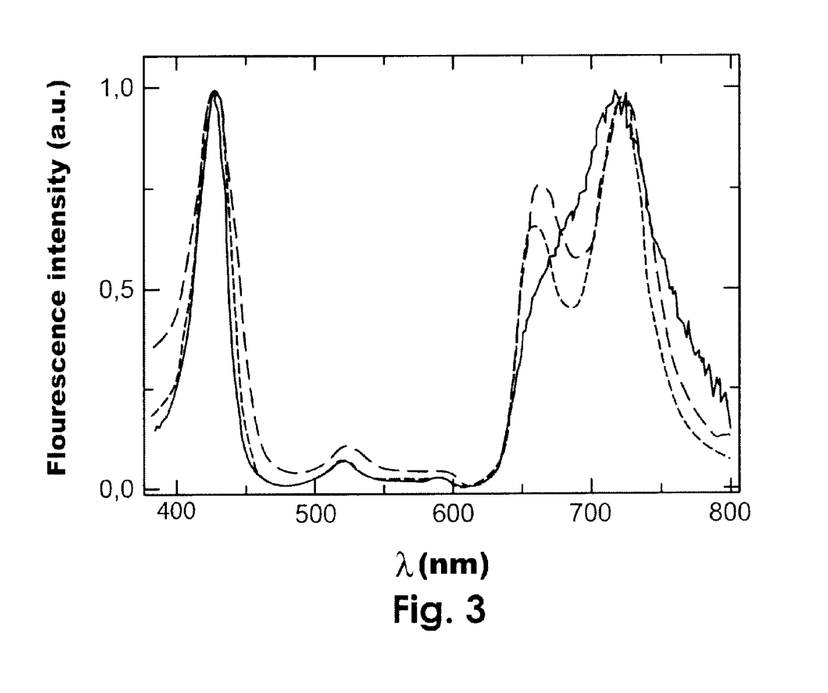
FIG. 3 is a graph showing the normalized fluorescence emission (above 600 nm) and excitation (below 600 nm) spectra of $T_4MPyP$ (solid line), the C18 derivative (dotted line), and the C22 derivative (dashed line) ca. 5 μM in phosphate buffered solution ("PBS") at pH 7.4.

The fluorescence spectrum of $T_4MPyP$ in buffer solution, pH 7.4, exhibited a maximum at 715 n with a shoulder at 675 nm (see FIG. 3). In general, an enhancement of the blue-shoulder was observed upon increasing the size of the alkyl tail. For the C18- and C22-derivatives, the fluorescence spectrum exhibited two maxima (at 660 and 720 nm). The excitation spectra, recorded at several emission wavelengths for the different porphyrin derivatives, always overlapped the corresponding absorption spectra. Only in the case of the C18 and C22 derivatives, an appreciable narrowing of the Soret band was observed in the excitation spectrum, which suggests that the fluorescence emission is mainly due to the monomeric component. This agrees with literature data. Table 1 shows the fluorescence quantum yields obtained for the various porphyrins in PBS and 2% aqueous SDS media. Such yields are predominantly below 0.03. This appears to indicate that the radiative decay from the first excited singlet state is of minor importance among the competitive relaxation processes. For most porphyrins, the quantum yield was found to be slightly higher in the micellar aqueous solution.

TABLE 1

Fluorescence quantum yields ($\Phi_F$) of $T_4MPyP$ and its analogues in PBS and in aqueous 2% SDS.

| PORPHYRIN | $\Phi_F$ (PBS) | $\Phi_F$ (SDS) |
|---|---|---|
| $T_4MPyP$ | 0.017 | 0.031 |
| C6 | 0.018 | 0.029 |
| C10 | 0.015 | 0.026 |
| C14 | 0.019 | 0.022 |
| C18 | 0.022 | 0.024 |
| C22 | 0.001 | 0.029 |

In particular, one can see that the $\phi_F$ value for the C22 derivative in PBS was much smaller than that recorded for the other porphyrins in the same medium while it became comparable to the other $\phi_F$ values in SDS. This behavior is likely to reflect the low solubility of the C22 derivative in a neutral aqueous solution leading to the formation of aggregates which are then disrupted by the addition of the SDS surfactant.

The fluorescence decay times were measured by the phase shift method, recording the total emitted light. The results of the global analysis of the frequency response curves are summarized in Table 2:

TABLE 2

Fluorescence decay times of porphyrins (ca. 5 $\mu$M) in air-equilibrated solutions buffered at pH 7.4. The data were obtained by the phase-shift method ($\lambda_{exc}$ = 420 nm, $\lambda_{em}$ > 600 nm).

| PORPHYRIN | $\tau_1$ (ns) | $A_1$ (%) | $\tau_2$ (ns) | $A_2$ (%) |
|---|---|---|---|---|
| $T_4MPyP$ | 1.0 | 29 | 4.7 | 71 |
| C6 | 0.9 | 6 | 5.1 | 94 |
| C10 | 1.1 | 6 | 5.2 | 94 |
| C14 | 1.0 | 2 | 6.5 | 98 |
| C18 | 1.4 | 3 | 9.0 | 97 |
| C22 | 0.5 | 27 | 5.9 | 73 |

For all the porphyrin derivatives, the frequency response traces were satisfactorily fitted by a bi-exponential function. The analysis of the $T_4$ MPYP curves gave a decay time ($\tau_1$) of 1.0 ns and a relative weight of 29% for the fast component, while a decay time ($\tau_2$) Of 4.7 ns was obtained for the slow component. The comparison of the present results with literature data suggests the assignment of the long- and short-lived species to the monomer and dimer of the porphyrin derivatives, respectively. The analysis of the traces obtained for the C6-, C10-, C14- and C18-derivatives gave decay times similar, within experimental errors, to those obtained for $T_4MPyP$; however, the relative contribution of the fast component of the alkyl-derivatives was about one order of magnitude smaller (2–6%) than that obtained for the model compound. For the C22-derivative, the fast component showed a decay time of 0.5 ns and a relative weight of ca. 30%. The different fit of the parameters together with the changes observed in the absorption and emission spectra of C22 might indicate the occurrence of new deactivation paths or interaction processes.

Example 10

Triplet State Properties

Figure 4:
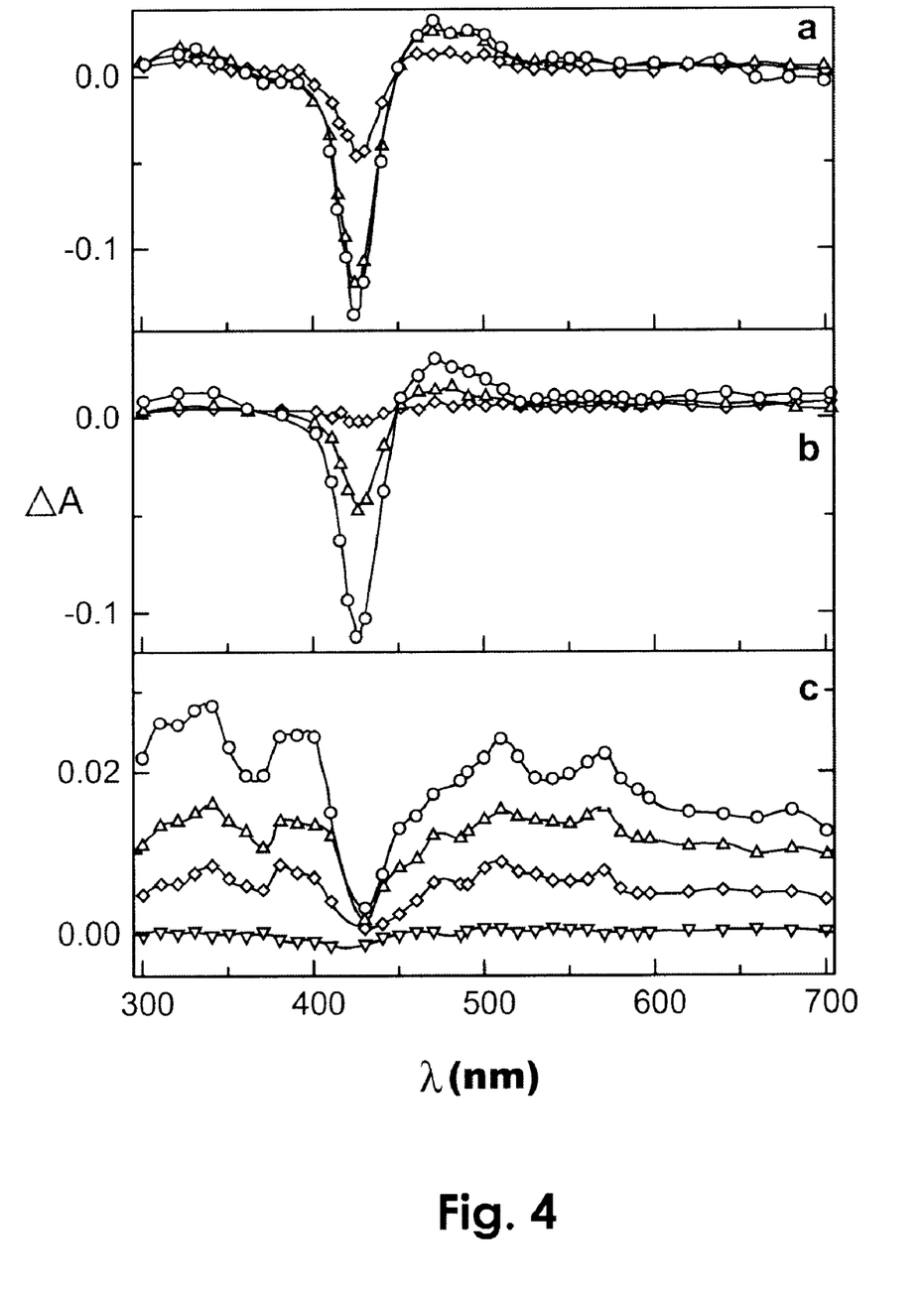
FIG. 4 is a graph showing the transient absorption spectra of the porphyrin derivatives in air-equilibrated phosphate buffered solution at pH=7.4), ($\lambda_{exc}$=420 nm): (a) $T_4MPyP$ with delay times of 1.0 (○), 8.0 (Δ) and 80(◇) μs; (b) the C18 derivative with delay times of 0.2 (○), 2.0 (Δ) and 6.0 (◇) μs; and (c) the C22 derivative with delay times of 0.05 (○), 0.12 (Δ) 0.24 (◇) and 1.6 (▽) μs.

The transient spectra of the porphyrins in buffer solutions were recorded upon laser flash photolysis excitation at 355 and 420 nm. The time-resolved spectra of $T_4MPyP$ (see FIG. 4a) displayed a maximum at 480 nm and a negative minimum at 425 nm (corresponding to the ground state absorption) due to the triplet—triplet absorption. The decay (growth) of the signal (bleaching) occurred according to first-order kinetics and led to a complete recovery of the ground state with a lifetime of 91 $\mu$s. Taking into account the known absorption coefficient of the ground state at 425 nm, the total depletion method was used to obtain the triplet—triplet absorption coefficient of the porphyrin at 920 nm ($\epsilon_T$), where the ground state does not significantly contribute to absorption. This also allowed the triplet quantum yield ($\phi_T$) to be determined (see Table 3), after calibration of the experimental setup by use of an optically-matched solution of benzophenone in acetonitrile.

TABLE 3

Triplet properties of porphyrins in phosphate-buffered solutions.

| PORPHYRIN | $\lambda_{min}$ (nm) | $\lambda_{max}$ (nm) | $\tau^{N2}$ ($\mu$s) | $\tau^{air}$ ($\mu$s) | $\phi \times \epsilon_{920}$ (M$^{-1}$ cm$^{-1}$) | $\phi_T^a$ |
|---|---|---|---|---|---|---|
| $T_4MPyP$ | 425 | 480 | 91 | 14 | 6814 | 0.73 |
| C6 | 425 | 480 | 71 | 16 | 6217 | 0.48 |
| C10 | 420 | 490 | 67 | 20 | 10214 | 0.49 |
| C14 | 425 | 480 | 70 | 20 | 9762 | 0.48 |
| C18 | 420 | 470 | 74 | 21 | 2700 | 0.17 |
| C22 | 420 | 340, 510 | n.d.$^b$ | 0.1 | <122 | <0.08 |

$^a$Tripet quantum yields determined by estimating the $\epsilon_{920}$ by total depletion method (from the $\epsilon$ of the ground state).
$^b$Non detected since the solution bubbled with $N_2$ produces a lot of foam and the substrate is concentrated on the cuvette walls.

$^a$ Triplet quantum yields determined by estimating the $\epsilon_{920}$ by total depletion method (from the $\epsilon$ of the ground state).

$^b$ Non detected since the solution bubbled with $N_2$ produces a lot of foam and the substrate is concentrated on the cuvette walls.

For T4 MPyP a $\phi_T$ value of 0.73 was obtained which is slightly lower than the literature values. This disagreement is probably due to the presence of partially aggregated porphyrin species, as suggested by the fluorescence decay data (see Table 2). Laser flash photolysis experiments with C6 to C18 porphyrin derivatives gave a transient species which was assigned to the lowest triplet state owing to the similarity of the spectral and decay properties with those recorded for T4 MPyP. This is exemplified for the C18-derivative in FIG. 4b. On the other hand, in the case of the C22-derivative the transient spectrum exhibited different absorption maxima at 340 and 510 nm (FIG. 4c) and a shorter decay time of 0.1 $\mu$s (see Table 3). As shown in the Table, the triplet quantum yield was influenced by the length of the N-alkyl chain and showed a marked decrease for C18 and even more for C22.

In the case of C22, the shortening of the triplet lifetime likely reflects the formation of extensively aggregated C22 species, as suggested by both the broadening of the absorption spectrum in the blue wavelength region, and the apparent low contribution of the slow- and fast-decaying components to the overall fluorescence emission of this porphyrin sample. A much smaller influence was exerted by the N-substituent on the triplet lifetime (see Table 3), even though such lifetime was quenched by the presence of oxygen, as is typical of photodynamic photosensitizers. The hypothesis that aggregation is mainly responsible for the poor photophysical properties of C22 receives further support by the observation that its photosensitizing activity toward NATA, which is negligible in phosphate-buffered aqueous solution, becomes very similar with that typical of the other porphyrins in the presence of SDS micelles (see Hydrophobicity Example 3, Table 4). This surfactant is known to induce the monomerization of aggregated porphyrin species.

Example 11

Photosensitization Studies of N-acetyl-L-tryptophanamide and Porphyrin Photobleaching The intrinsic photosensitizing efficiency of the various porphyrins was tested against NATA as a model substrate. Tryptophan is known to undergo a photosensitized modification of its indole moiety by both type I (radical-involving) and type 11 ($^1O_2$-involving) pathways (Foote, *Oxygen and Oxy-Radicals in Chemistry and Biology*, 425–440 (1981)), hence it can be used to test the activity of photosensitizing agents independently of the actual reaction mechanism.

As shown in Table 4, both $T_4MPyP$ and all of its analogs with longer alkyl chains induced a readily detectable photooxidative degradation of NATA with quantum yield values in the $10^{-3}$ range, as previously found for other photosensitizers. Foote, Oxygen and *Oxy-Radicals in Chemistry and Biology*, 425–440 (1981).

TABLE 4

Quantum yields ($\Phi$) for the photo-oxidation of 10 $\mu$M NATA sensitized by the different porphyrin derivatives in phosphate buffered solution and in aqueous 2% SDS.

| PORPHYRIN | $\Phi_{PBS} \times 10^3$ | $\Phi_{SDS} \times 10^3$ |
|---|---|---|
| $T_4MPyP$ | 0.77 ± 0.21 | 0.64 ± 0.08 |
| C6 | 0.59 ± 0.05 | 0.68 ± 0.14 |
| C10 | 0.59 ± 0.05 | 0.64 ± 0.26 |
| C14 | 0.66 ± 0.10 | 0.71 ± 0.03 |
| C18 | 0.14 ± 0.01 | 0.80 ± 0.04 |
| C22 | n.d.$^a$ | 0.83 ± 0.08 |

$^a$Non-detectable

Only minor changes in the quantum yield were measured for the various porphyrin derivatives in 2% aqueous SDS solutions, where all the samples were in a pure monomeric form. It is clearly demonstrated that the formation of aggregates brings about a drastic effect on the photosensitizing efficiency of porphyrins, as is shown by the quantum yield values for NATA photooxidation in PBS (see Table 4). Such values are closely similar to those found in 2% SDS for the $T_4MPyP$ and C14-derivatives, which exist in a largely monomeric state in both media, while a drop to below our detection limits is observed for C22, which is heavily aggregated in a neutral homogeneous aqueous solution.

Figure 5:
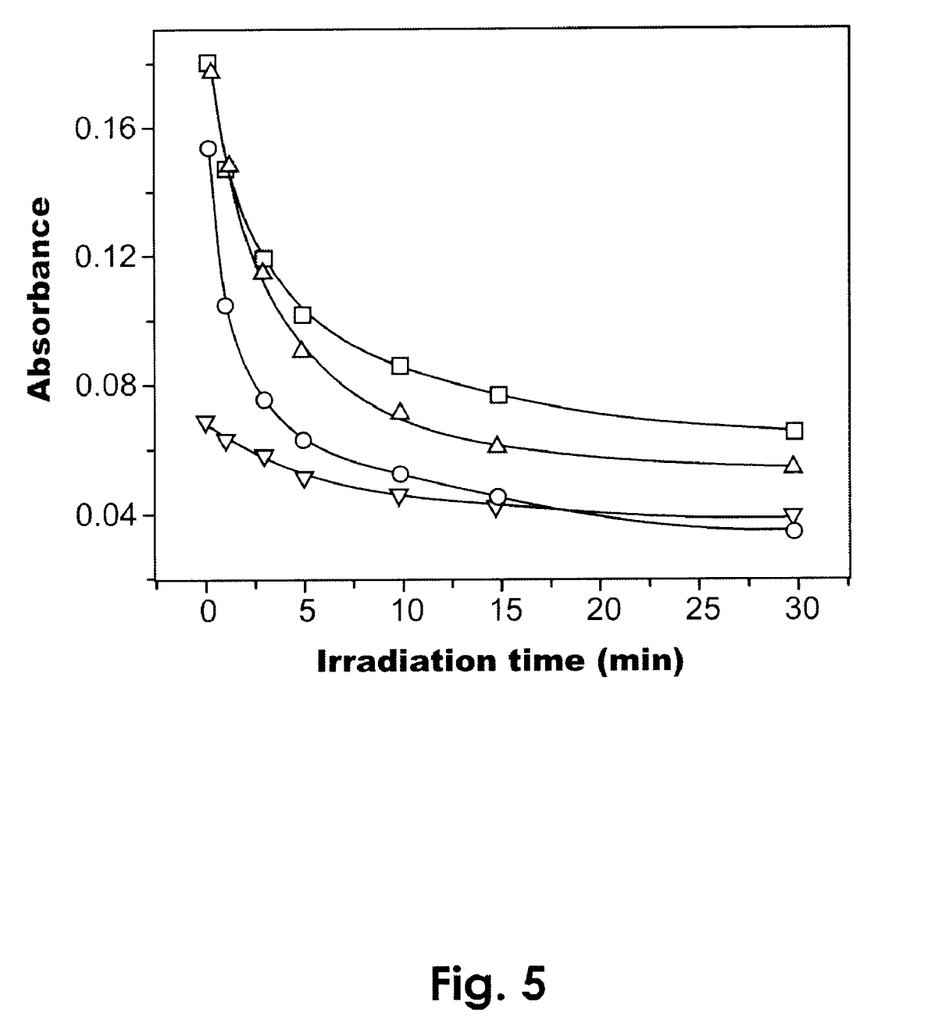
FIG. 5 is a graph showing the photobleaching of the porphyrin derivatives following irradiation with white light for different periods. The porphyrin bleaching was monitored by measuring the decrease of absorbance at the maximum of the Soret band: 422 nm $T_4MPyP$ (■), 423 nm C10 (●), 424 nm C14 (▲) and 432 nm C22 (▼).

As shown in FIG. 5, all the porphyrins underwent a gradual photobleaching when 1 $\mu$M solutions in PBS were irradiated with white light. In all cases, the photo-induced decrease in porphyrin concentration was fitted by a bi-exponential plot: the initial fast degradation phase was most often characterized by $t^{1/2}$ between 1 and 3 min; however, the C22 derivative sample appeared to be markedly more photostable ($t^{1/2}$=6.5 min.).

Example 12

Binding of Porphyrins to Bacteria Cells

Figure 6:
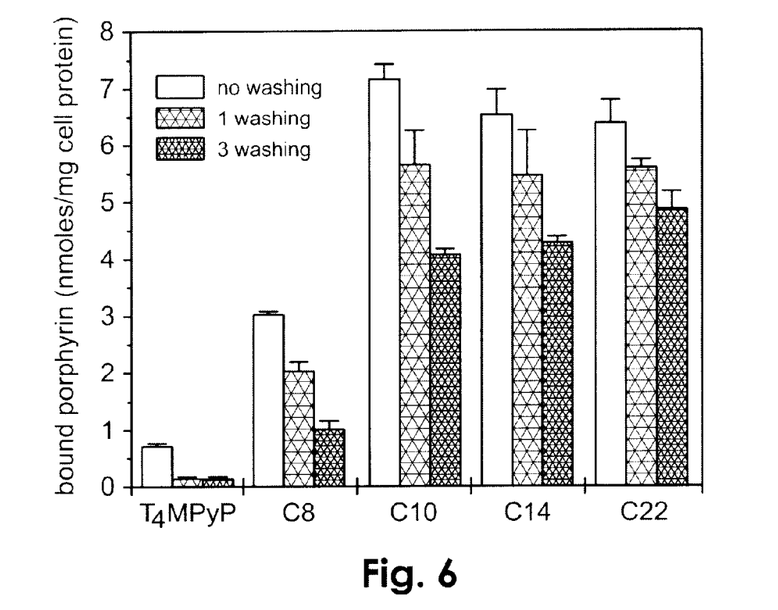
FIG. 6 is a graph showing the binding of $T_4MPyP$ and its analogues to *S. aureus* cells. The amount of cell-bound porphyrin was determined after 5 min. incubation with 1 μM porphyrin at room temperature without washing the cells, and after 1 and 3 washing steps with PBS.
Figure 7:
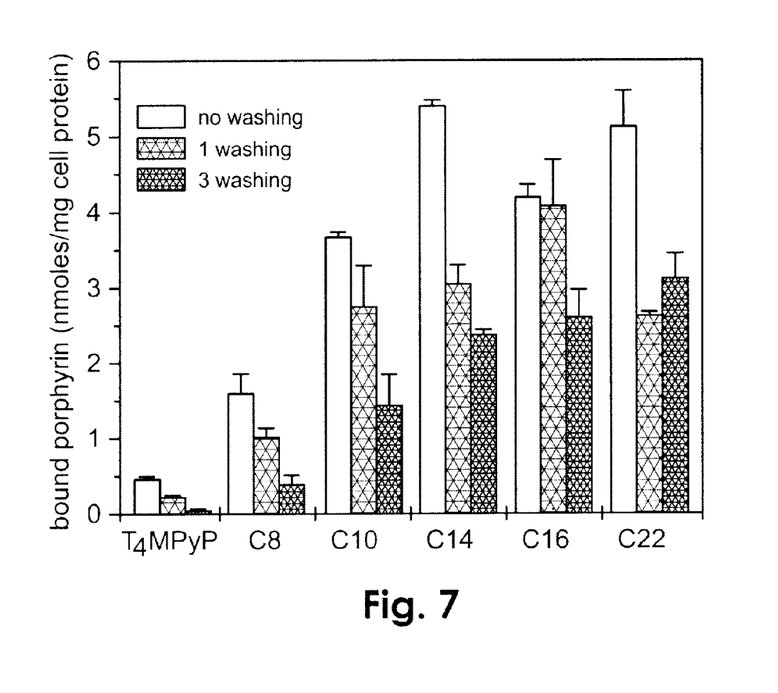
FIG. 7 is a graph showing the binding of $T_4MPyP$ and its analogues to *E. coli* cells. The experimental conditions are identical to those in FIG. 6.
Figure 8:
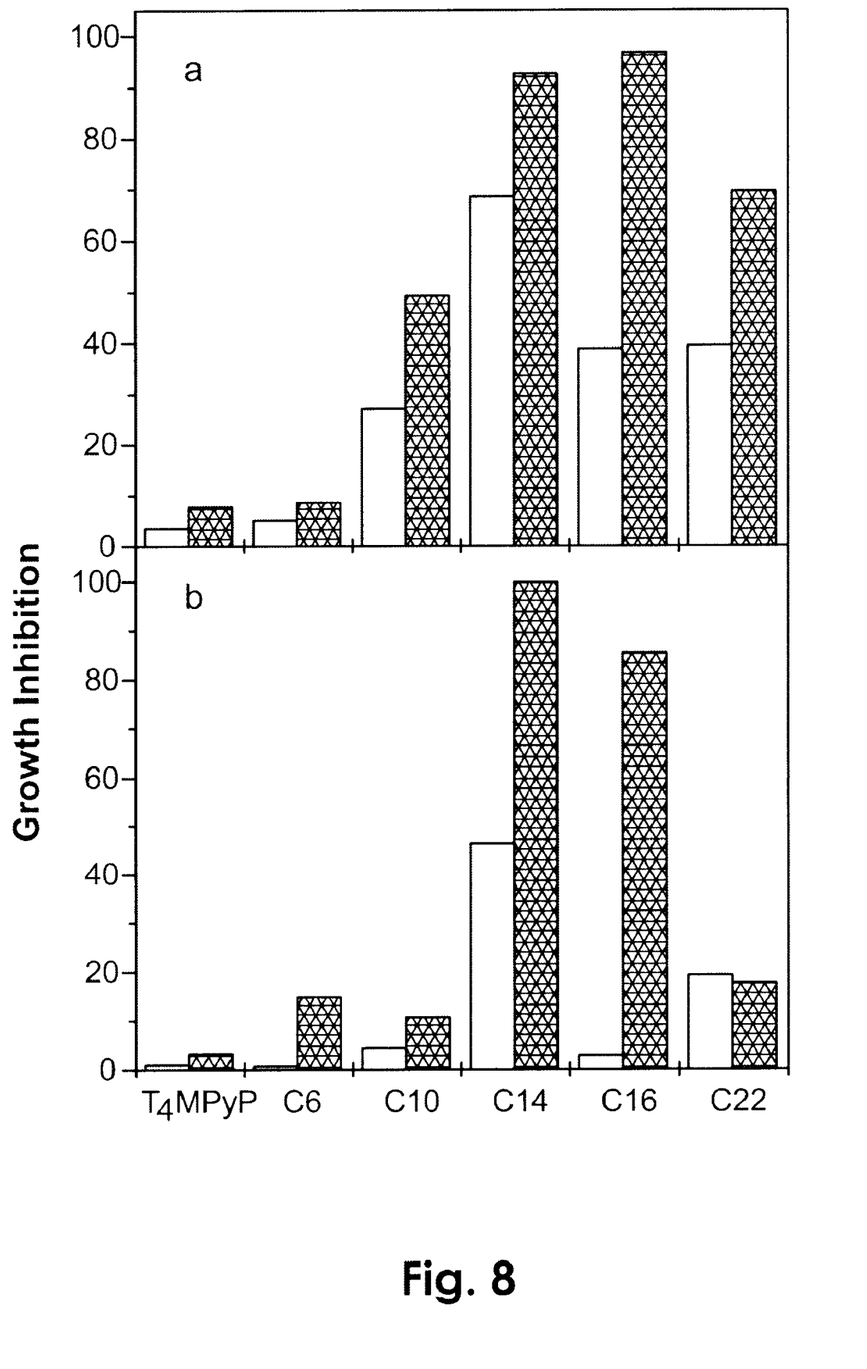
FIG. 8 is a graph showing the growth inhibition of *S. aureus* (a) and *E. coli* cells (b) exposed for 5 min. to 1 (white column) or 10 μM (gray column) porphyrin in the dark.

The binding of $T_4MPyP$ and its analogues to *S. aureus* and *E. coli* cells is shown in FIGS. 6 and 7, respectively. Clearly, increasing the length of the N-alkyl substituent from 1 to 10 carbon atoms enhanced the efficiency of porphyrin accumulation by both Gram-positive and Gram-negative bacteria. A further elongation of the alkyl chain to C14 and C22 had no important effect on the amount of cell-bound porphyrin. In particular, the amount of C10–C22 porphyrins associated to unwashed bacteria cells was ca 10-fold higher in comparison to $T_4$MPyP. In all cases, the porphyrin binding was higher in the case of S. aureus cells. The lower affinity of porphyrins for E. coli cells was particularly evident for the C6 and C10 derivatives whose association with S. aureus was almost two-fold larger than that found in the case of the Gram-negative bacterium.

A fraction of the cell-bound porphyrin could be gradually removed by repeated washing, suggesting that some porphyrin molecules were weakly bound to the cells. However, as the hydrophobicity of the photosensitizer increased, the aliquot which was still associated to the cells after one or three washings substantially increased: thus, E. coli and S. aureus cells, subjected to three washings after 5 min incubation with $T_4$MPyP, retained only 11% and 16%, respectively, of the initially bound porphyrin. These percentages increased up to about 60% for E. coli and 77% for S. aureus when the bacteria cells were incubated with porphyrin derivatives bearing a substituent with 10–22 carbon atoms. This implies that the amount of porphyrin tightly associated to bacteria was 50–60 times larger than that observed in the case of $T_4$MPyP.

Example 13

Dark- and Photo-Toxicity of Porphyrins on Bacterial Cells

The cytotoxic action of the various porphyrin derivatives on bacterial cells was assessed after 5 min incubation in the dark. The data presented in FIG. 8a for S. aureus and in FIG. 8b for E. coli pointed out that the degree of dark cytotoxicity for both bacterial strains was strongly dependent on the chemical structure of the photosensitizing agent. Thus, a 10 $\mu$M concentration of either $T_4$MPyP or the C6-derivative caused a barely detectable inhibition of bacterial cell growth, while a complete inhibition was induced by the incubation with 10 $\mu$M C14- or C18-derivatives. The observed effect appeared to be mostly of bacteriostatic rather than bactericidal nature, at least against E. coli, since only a modest (less than 2 logs) decrease in cell survival was observed following cell incubation with 10 $\mu$M C14 or C18. In all cases, the "dark" cytotoxic effect was markedly more pronounced against S. aureus as compared with E. coli (see FIG. 8).

All the porphyrins examined were also efficient photosensitizers for the damage of S. aureus and E. coli cells at concentrations which had essentially no effect in the dark. As one can see in Table 5, an appreciable inhibition of cell growth was observed for both S. aureus and E. coli upon irradiation in the presence of 10 $\mu$M $T_4$MPyP and C6.

TABLE 5

Growth inhibition of E. coli and S. aureus cells irradiated for 5 min with white light (150 mW/cm$^2$) after 5 min incubation with the various porphyrins at 0.5–10 $\mu$M concentrations.

| PORPHYRIN | CONCENTRATION ($\mu$M) | GROWTH INHIBITION (%) E. coli | S. aureus |
|---|---|---|---|
| $T_4$MPyP | 10 | 29 | 96 |
| C6 | 0.5 | 5 | 47 |
|  | 10 | 99 | — |
| C10 | 0.5 | 46 | 74 |
|  | 1 | 96 | — |
| C14 | 0.5 | 82 | 73 |
|  | 1 | 100 | — |
| C18 | 0.5 | 26 | 42 |
|  | 1 | 58 | 59 |
| C22 | 0.5 | — | 27 |
|  | 1 | 3 | 70 |

The antimicrobial photoactivity of the porphyrins increased upon increasing the length of the N-alkyl chain to C10 and C14, which caused a complete growth inhibition of E. coli at doses as low as 1 $\mu$M. A further increase of the substituent size to C18 and C22 was accompanied by a drop in the photosensitizing efficiency, which was especially evident in the case of E. coli. This bacterial strain, which appeared to be generally more photoresistant than S. aureus, was also assayed for any loss of viability as a consequence of porphyrin photosensitization. As shown in Table 6, the survival data closely paralleled the growth inhibition data.

TABLE 6

Decrease of survival of E. coli cells irradiated for 15 min with white light (150 mW/cm$^2$) after incubation for 5 min in the dark with 1 or 10 $\mu$M porphyrin.

| PORPHYRIN | DECREASE OF SURVIVAL (log) 1 $\mu$M | 10 $\mu$M |
|---|---|---|
| T4MpyP | +0.28 | −1.82 ± 0.82 |
| C6 | +0.05 | −4.23 ± 0.54 |
| C10 | −4.32 ± 0.34 | — |
| C14 | −4.35 ± 0.45 | — |
| C18 | −2.78 ± 0.62 | — |
| C22 | +0.22 ± 0.07 | −1.94 ± 0.28 |

Maximum photoefficiency was actually observed for C10- and C14-derivatives, which caused a 4 log drop in survival of E. coli cells upon 15 min. irradiation in the presence of 1 $\mu$M porphyrin. A similar result was obtained with C6 only for 10 $\mu$M concentrations, while a lower efficiency was exhibited by both $T_4$MPyP and C22 derivatives.

Thus, the present invention includes a group of novel positively-charged porphyrins with up to four positive charges which include a hydrophobic hydrocarbon chain. The hydrocarbon tail may include at least one hydrocarbon chain of six to 22 carbons in length. The tail may include a straight chain alkyl, a straight chain alkene, a branched alkyl chain, a branched alkenyl chain, an aromatic, a mixed alkyl-aromatic species, and a mixed alkenyl-aromatic species.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by United States Letters Patent is:

1. A photodynamic antimicrobial agent comprising:
a porphyrin having four quaternized nitrogens, wherein the porphyrin further comprises a hydrocarbon tail beginning at one of the quaternized nitrogens and having between 6 and 22 carbon atoms.

2. The photodynamic antimicrobial agent of claim 1, wherein the porphyrin is a reduced porphyrin.

3. The photodynamic antimicrobial agent of claim 2, wherein the reduced porphyrin is selected from the group consisting of chlorin and bacteriochlorin.

4. The photodynamic antimicrobial agent of claim 1, wherein the porphyrin is a metal chelated porphyrin.

5. The photodynamic antimicrobial agent of claim 4, wherein the metal chelated porphyrin is a metal chelate of a metal selected from the group consisting of Mg, Sc, Zn, Al, In, Tl, Si, Ge, Sn, Pd, and Pt.

6. The photodynamic antimicrobial agent of claim 2, wherein the porphyrin is a metal chelated porphyrin.

7. The photodynamic antimicrobial agent of claim 6, wherein the metal chelated porphyrin is a metal chelate of a metal selected from the group consisting of Mg, Sc, Zn, Al, In, Tl, Si, Ge, Sn, Pd, and Pt.

8. The photodynamic antimicrobial agent of claim 1, wherein the hydrocarbon tail is selected from the group consisting of straight chain alkyls, straight chain alkenes, branched alkyl chains, branched alkenyl chains, aromatics, mixed alkyl-aromatic species, and mixed alkenyl-aromatic species.

9. The photodynamic antimicrobial agent of claim 1, wherein the hydrocarbon tail contains between 6 and 18 carbon atoms.

10. The photodynamic antimicrobial agent of claim 9, wherein the hydrocarbon tail comprises a benzyl group.

11. The photodynamic antimicrobial agent of claim 9, wherein the hydrocarbon tail comprises a six-carbon atom chain.

12. The photodynamic antimicrobial agent of claim 9, wherein the hydrocarbon tail comprises a ten-carbon atom chain.

13. The photodynamic antimicrobial agent of claim 9, wherein the hydrocarbon tail comprises a fourteen-carbon atom chain.

14. The photodynamic antimicrobial agent of claim 9, wherein the hydrocarbon tail comprises an eighteen-carbon atom chain.

15. A photodynamic antimicrobial agent comprising a meso-tetra-(N-methyl-pyridyl) porphyrin having four quaternized nitrogens, and wherein one N-methyl group has been replaced by a hydrocarbon tail having between 6 and 22 carbon atoms.

16. The photodynamic antimicrobial agent of claim 15, wherein the hydrocarbon tail contains greater than 6 and fewer than 18 carbon atoms.

17. The photodynamic antimicrobial agent of claim 15, wherein the porphyrin is a reduced porphyrin.

18. The photodynamic antimicrobial agent of claim 17, wherein the reduced porphyrin is selected from the group consisting of chlorin and bacteriochlorin.

19. The photodynamic antimicrobial agent of claim 15, wherein the porphyrin is a metal chelated porphyrin.

20. The photodynamic antimicrobial agent of claim 19, wherein the metal chelated porphyrin is a chelate of a metal selected from the group consisting of Mg, Sc, Zn, Al, In, Tl, Si, Ge, Sn, Pd, and Pt.

21. The photodynamic antimicrobial agent of claim 17, wherein the porphyrin is a metal chelated porphyrin.

22. The photodynamic antimicrobial agent of claim 21, wherein the metal chelated porphyrin is a metal chelate of a metal selected from the group consisting of Mg, Sc, Zn, Al, In, Tl, Si, Ge, Sn, Pd, and Pt.

23. The photodynamic antimicrobial agent of claim 15, wherein the hydrocarbon tail is selected from the group consisting of straight chain alkyls, straight chain alkenes, branched alkyl chains, branched alkenyl chains, aromatics, mixed alkyl-aromatic species, and mixed alkenyl-aromatic species.

24. The photodynamic antimicrobial agent of claim 23, wherein the hydrocarbon tail comprises a benzyl group.

25. The photodynamic antimicrobial agent of claim 23, wherein the hydrocarbon tail comprises a six-carbon atom chain.

26. The photodynamic antimicrobial agent of claim 23, wherein the hydrocarbon tail comprises a ten-carbon atom chain.

27. The photodynamic antimicrobial agent of claim 23, wherein the hydrocarbon tail comprises a fourteen-carbon atom chain.

28. The photodynamic antimicrobial agent of claim 23, wherein the hydrocarbon tail comprises an eighteen-carbon atom chain.

29. A method of synthesizing porphyrins with four symmetrically distributed positive charges on four quaternized nitrogens and a single hydrophobic hydrocarbon tail comprising the steps of:
quaternizing a first nitrogen of a porphyrin by reacting it with a sub-stoichiometric quantity of a halide salt of the desired hydrophobic hydrocarbon tail to form a mono-quaternized porphyrin; and
quaternizing the remaining nitrogens of the porphyrin using a methylating agent to form a porphyrin with four symmetrically distributed positive charges on four quaternized nitrogens and a single hydrophobic tail.

30. The method of synthesizing porphyrins with four symmetrically distributed positive charges on four quaternized nitrogens and a single hydrophobic tail of claim 29, further comprising the step of separating the mono-quaternized porphyrin from any remaining porphyrin or halide salts.

31. The method of synthesizing porphyrins with four symmetrically distributed positive charges on four quaternized nitrogens and a single hydrophobic hydrocarbon tail of claim 30, wherein the step of separating the mono-quaternized porphyrin from any remaining porphyrin or halide salts is accomplished utilizing solubility differences.

32. The method of synthesizing porphyrins with four symmetrically distributed positive charges on four quaternized nitrogens and a single hydrophobic tail of claim 30, further comprising the step of separating the resulting porphyrin with four symmetrically distributed positive charges and a single hydrophobic hydrocarbon tail from any remaining porphyrins, other byproducts, and halide salts.

33. The method of synthesizing porphyrins with four symmetrically distributed positive charges on four quaternized nitrogens and a single hydrophobic hydrocarbon tail of claim 32, wherein the step of separating the resulting porphyrin with four symmetrically distributed positive charges and a single hydrophobic hydrocarbon tail from any remaining porphyrins, other byproducts, and halide salts is accomplished using chromatography.

34. The method of synthesizing porphyrins with four symmetrically distributed positive charges on four quaternized nitrogens and a single hydrophobic hydrocarbon tail of claim 32, wherein the halide salt is selected from the group consisting of a straight chain alkyl, straight chain alkene, branched alkyl, branched alkenyl, aromatic, mixed alkyl-aromatic, or mixed alkenyl-aromatic halide salt.

35. The method of synthesizing porphyrins with four symmetrically distributed positive charges on four quaternized nitrogens and a single hydrophobic hydrocarbon tail of claim 32, wherein the methylating agent is selected from the group consisting of methyl-p-toluene sulformate, methyl iodide, dimethyl sulfate, and methyl fluorosulfonate.

36. The method of synthesizing porphyrins with four symmetrically distributed positive charges on four quaternized nitrogens and a single hydrophobic hydrocarbon tail of claim 32, wherein the porphyrin is a reduced porphyrin.

37. The method of synthesizing porphyrins with four symmetrically distributed positive charges on four quaternized nitrogens and a single hydrophobic hydrocarbon tail of claim 36, wherein the reduced porphyrin is selected from the group consisting of chlorin and bacteriochlorin.

38. The method of synthesizing porphyrins with four symmetrically distributed positive charges on four quaternized nitrogens and a single hydrophobic hydrocarbon tail of claim 32, wherein the porphyrin is a metal chelated porphyrin.

39. The method of synthesizing porphyrins with four symmetrically distributed positive charges on four quaternized nitrogens and a single hydrophobic hydrocarbon tail of claim 38, wherein the metal chelated porphyrin is a metal chelate of a metal selected from the group consisting of Mg, Sc, Zn, Al, In, Tl, Si, Ge, Sn, Pd, and Pt.

40. The method of synthesizing porphyrins with four symmetrically distributed positive charges on four quaternized nitrogens and a single hydrophobic hydrocarbon tail of claim 36, wherein the porphyrin is a metal chelated porphyrin.

41. The method of synthesizing porphyrins with four symmetrically distributed positive charges on four quaternized nitrogens and a single hydrophobic hydrocarbon tail of claim 40, wherein the metal chelated porphyrin is a metal chelate of a metal selected from the group consisting of Mg, Sc, Zn, Al, In, Tl, Si, Ge, Sn, Pd, and Pt.

42. A method of killing Gram-positive or Gram-negative bacteria comprising the steps of:
exposing Gram-positive or Gram-negative bacteria to a photodynamic antimicrobial agent comprising a porphyrin with four symmetrically-distributed positive charges and a hydrocarbon tail having between 6 and 22 carbon atoms; and
irradiating the bacteria and antimicrobial agent.

43. The method of claim 42, wherein the porphyrin is a reduced porphyrin.

44. The method of claim 43, wherein the reduced porphyrin is selected from the group consisting of chlorin and bacteriochlorin.

45. The method of claim 44, wherein the porphyrin is a metal chelated porphyrin.

46. The method of claim 45, wherein the metal chelated porphyrin is a chelate of a metal selected from the group consisting of Mg, Sc, Zn, Al, In, Ti, Si, Ge, Sn, Pd, and Pt.

47. The method of claim 43, wherein the porphyrin is a metal chelated porphyrin.

48. The method of claim 47, wherein the metal chelated porphyrin is a metal chelate of a metal selected from the group consisting of Mg, Sc, Zn, Al, In, Tl, Si, Ge, Sn, Pd, and Pt.

49. The method of claim 42, wherein the hydrocarbon tail is selected from the group consisting of straight chain alkyls, straight chain alkenes, branched alkyl chains, branched alkenyl chains, aromatics, mixed alkyl-aromatic species, and mixed alkenyl-aromatic species.

50. The method of claim 42, wherein the hydrocarbon tail contains greater than 6 and fewer than 18 carbon atoms.

51. The method of claim 50, wherein the hydrocarbon tail comprises a benzyl group.

52. The method of claim 50, wherein the hydrocarbon tail comprises a six-carbon atom chain.

53. The method of claim 50, wherein the hydrocarbon tail comprises a ten-carbon atom chain.

54. The method of claim 50, wherein the hydrocarbon tail comprises a fourteen-carbon atom chain.

55. The method of claim 50, wherein the hydrocarbon tail comprises an eighteen-carbon atom chain.

56. The method of claim 42, wherein the porphyrin is present in a concentration of from about 10 $\mu$M to about 0.1 $\mu$M.

57. The method of claim 42, wherein the porphyrin is present in a concentration of from about 5 $\mu$M to about 0.5 $\mu$M.

58. The method of claim 42, wherein the porphyrin is present in a concentration of 1 $\mu$M.

* * * * *